United States Patent
Nakari-Setälä et al.

(10) Patent No.: US 7,338,779 B1
(45) Date of Patent: Mar. 4, 2008

(54) METHOD FOR DECREASING THE FOAM FORMATION DURING CULTIVATION OF A MICROORGANISM

(75) Inventors: Tiina Nakari-Setälä, Espoo (FI); Merja Penttilä, Helsinki (FI); Michael Bailey, Espoo (FI); Maija Tenkanen, Espoo (FI)

(73) Assignee: Valtion Teknillinen Tutkimuskeskus, VVT (FI)

( * ) Notice: Subject to any disclaimer, the term of this patent is extended or adjusted under 35 U.S.C. 154(b) by 470 days.

(21) Appl. No.: 10/050,000

(22) PCT Filed: Aug. 21, 2000

(86) PCT No.: PCT/FI00/00707

§ 371 (c)(1),
(2), (4) Date: May 3, 2002

(87) PCT Pub. No.: WO01/14521

PCT Pub. Date: Mar. 1, 2001

(30) Foreign Application Priority Data

Aug. 20, 1999 (FI) .................................. 19991781

(51) Int. Cl.
*C12P 39/00* (2006.01)
(52) U.S. Cl. ....................................... 435/42
(58) Field of Classification Search ................. 435/245, 435/246, 440
See application file for complete search history.

(56) References Cited

FOREIGN PATENT DOCUMENTS

WO 96/41882 A1 12/1996
WO 98/22598 A1 5/1998

OTHER PUBLICATIONS

Wosten et al. "Interfacial self-assembly of a fungal hydrophobin into a hydrophobic rodlet layer". The Plant Cell, Nov. 1993, vol. 5, pp. 1567-1574.*
Spanu et al. "Deletion of HCF-a, a hydrophobin gene of Cladosporium fulvum, does not affect pathogenicity on tomato". May 1998, vol. 52, No. 5, pp. 323-334.*
Razafindralambo et al., JAOCS, vol. 73, No. 1, pp. 149-151 (1996).
D'Souza et al., Journal of Bateriology, vol. 175, No. 11, pp. 3502-3510 (1993).
Nakano et al., Mol Gen Genet, vol. 232, pp. 313-321 (1992).
Vollenbroich et al., Journal of Bacteriology, vol. 176, No. 2, pp. 395-400 (1994).
Tiina Nakari-Setala et al., Eur. J. Biochem. 235, 1996, pp. 248-255, XP002949769.
Tiina Nakari-Setala et al., Eur. J. Biochem. 248, 1997, pp. 415-423, XP002949768.

* cited by examiner

*Primary Examiner*—Robert B. Mondesi
(74) *Attorney, Agent, or Firm*—Birch, Stewart, Kolasch & Birch, LLP

(57) ABSTRACT

This invention relates to a method for decreasing the foam formation during cultivation of a microorganism and to a method for producing an enhanced amount of a product of interest. The method comprises that the microorganism is modified in such a way that the microorganism does not produce an essential amount of at least one of the proteins, polypeptides or peptides associated with foam formation during cultivation of the unmodified microorganism. In particular the method comprises that the microorganism is modified not to produce an essential amount of amphipathic or hydrophobic proteins, polypeptides or peptides.

17 Claims, 16 Drawing Sheets

*hfb1* genomic sequence (SEQ ID No 1)

```
TTTGTATGGC TGGATCTCGA AAGGCCCTTG TCATCGCCAA GCGTGGCTAA TATCGAATGA
GGGACACCGA GTTGCATATC TCCTGATCAT TCAAACGACA AGTGTGAGGT AGGCAATCCT
CGTATCCCAT TGCTGGGCTG AAAGCTTCAC ACGTATCGCA TAAGCGTCTC CAACCAGTGC
TTAGGTGACC CTTAAGGATA CTTACAGTAA GACTGTATTA AGTCAGTCAC TCTTTCACTC
GGGCTTTGAA TACGATCCTC AATACTCCG ATAACAGTAA GAGGATGATA CAGCCTGCAG
TTGGCAAATG TAAGCGTAAT TAAACTCAGC TGAACGGCCC TTGTTGAAAG TCTCTCTCGA
TCAAAGCAAA GCTATCCACA GACAAGGGTT AAGCAGGCTC ACTCTTCCTA CGCCTTGGAT
ATGCAGCTTG GCCAGCATCG CGCATGGCCA ATGATGCACC CTTCACGGCC CAACGGATCT
CCCGTTAAAC TCCCCTGTAA CTTGGCATCA CTCATCTGTG ATCCCAACAG ACTGAGTTGG
GGGCTGCGGC TGGCGGATGT CGGAGCAAAG GATCACTTCA AGAGCCCAGA TCCGGTTGGT
CCATTGCCAA TGGATCTAGA TTCGGCACCT TGATCTCGAT CACTGAGACA TGGTGAGTTG
CCCGGACGCA CCACAACTCC CCTGTGTCA TTGAGTCCCC ATATGCGTCT TCTCAGCGTG
CAACTCTGAG ACGGATTAGT CCTCACGATG AAATTAACTT CCAGCTTAAG TTCGTAGCCT
TGAATGAGTG AAGAAATTTC AAAAACAAAC TGAGTAGAGG TCTTGAGCAG CTGGGGTGGT
ACGCCCCTCC TCGACTCTTG GACATCGTA CGGCAGAGAA TCAACGGATT CACACCTTTG
GGTCGAGATG AGCTGATCTC GACAGATACG TGCTTCACCA CAGCTGCAGC TACCTTTGCC
CAACCATTGC GTTCCAGGAT CTTGATCTAC ATCACCGCAG CACCCGAGCC AGGACGGAGA
GAACAATCCG GCCACAGAGC AGCACCGCCT TCCAACTCTG CTCCTGGCAA CGTCACACAA
CCTGATATTA GATATCCACC TGGGTGATTG CCATTGCAGA GAGGTGGCAG TTGGTGATAC
CGACTGGCCA TGCAAGACGC GGCCGGGCTA GCTGAAATGT CCCCGAGAGG A<u>CAATTG</u>GGA
GCGTCTATGA CGGCGTGGAG ACGACGGGAA AGGACTCAGC CGTCATGTTG TGTTGCCAAT
TTGAGATTGT TGACCGGGAA AGGGGGGACG AAGAGGATGG CTGGGTGAGG TGGTATTGGG
AGGATGCATC ATTCGACTCA GTGAGCGATG TAGAGCTCCA AGAATATAAA TATCCCTTCT
CTGTCTTCTC AAAATCTCCT TCCATCTTGT CCTTCATCAG CACCAGAGCC AGCCTGAACA
CCTCCAGTCA ACTTCCCTTA CCAGTACATC TGAATCAACA TCCATTCTTT GAAATCTCAC
CACAACCACC ATCTTCTTCA AA<u>ATGAAGTT CTTCGCCATC GCCGCTCTCT TGCCGCCGC</u>
<u>TGCCGTTGCC CAGCCTCTCG AGGACCGCAG CAACGGCAAC GGCAATGTTT GCCCTCCCGG</u>
<u>CCTCTTCAGC AACCCCAGT GCTGTGCCAC CCAAGTCCTT GGCCTCATCG GCCTTGACTG</u>
<u>CAAAGTCCGT AAGTTGAGCC ATAACATAAG AATCCTCTTG ACGGAAATAT GCCTTCTCAC</u>
<u>TCCTTTACCC CTGAACAGCC TCCCAGAACG TTTACGACGG CACCGACTTC CGCAACGTCT</u>
<u>GCGCCAAAAC CGGCGCCCAG CCTCTCTGCT GCGTGGCCCC CGTTGTAAGT TGATGCCCCA</u>
<u>GCTCAAGCTC CAGTCTTTGG CAAACCCATT CTGACACCCA GACTGCAGGC CGGCCAGGCT</u>
<u>CTTCTGTGCC AGACCGCCGT CGGTGCTTGA</u> GATGCCCGCC CGGGGTCAAG GTGTGCCCGT
GAGAAAGCCC ACAAAGTGTT GATGAGGACC ATTTCCGGTA CTGGGAAAGT TGGCTCCACG
TGTTTGGGCA GGTTTGGGCA AGTTGTGTAG ATATTCCATT CGTACGCCAT TCTTATTCTC
CAATATTTCA GTACACTTTT CTTCATAAAT CAAAAGACT GCTATTCTCT TTGTGACATG
CCGGAAGGGA A<u>CAATTG</u>CTC TTGGTCTCTG TTATTTGCAA GTAGGAGTGG GAGATTCGCC
TTAGAGAAAG TAGAGAAGCT GTGCTTGACC GTGGTGTGAC TCGACGAGGA TGGACTGAGA
GTGTTAGGAT TAGGTCGAAC GTTGAAGTGT ATACAGGATC GTCTGGCAAC CCACGGATCC
TATGACTTGA TGCAATGGTG AAGATGAATG ACAGTGTAAG AGGAAAAGGA AATGTCCGCC
TTCAGCTGAT ATCCACGCCA ATGATACAGC GATATACCTC CAATATCTGT GGGAACGAGA
CATGACATAT TTGTGGGAAC AACTTCAAAC AGCGAGCCAA GACCTCAATA TGCACATCCA
AAGCCAAACA TTGGCAAGAC GAGAGACAGT CACATTGTCG TCGAAAGATG GCATCGTACC
CAAATCATCA GCTCTCATTA TCGCCTAAAC CACAGATTGT TTGCCGTCCC CCAACTCCAA
AACGTTACTA CAAAAGACAT GGGCGAATGC AAAGACCTGA AGCAAACCC TTTTTGCGAC
TCAATTCCCT CCTTTGTCCT CGGAATGATG ATCCTTCACC AAGTAAAAGA AAAAGAAGAT
TGAGATAATA CATGAAAAGC ACAACGGAAA CGAAAGAACC AGGAAAAGAA TAAATCTATC
ACGCACCTTG TCCCCACACT AAAAGCAACA GGGGGGGTAA AATGAAAT
```

Fig. 1

*hfb2* genomic sequence (SEQ ID No 2)

```
               HindIII
CTCGAGCAGC TGAAGCTTGC ATGCCTGCAT CCTTTGTGAG CGACTGCATC CATTTTGCAC
ACACTGCCGT CGACGTCTCT CTTCCGACCT TGGCCAGCTG GACAAGCAAC ACACCAATGA
CGCTTTGTAT TATTAGAGTA TATGCAAGTC TCAGGACTAT CGACTCAACT CTACCCACCG
AGGACGATCG CGGCACGATA CGCCCTCGTT CTCATTGGCC CAAGCAGACC AACTGCCCCT
GGAGCAAGAT TCAGCCCAAG GGAGATGGAC GGCAGGGCAC GCCAGGCCCC CACCACCAAG
CCACTCCCTT TGGCCAAATC AGCTTGCATG TCAAGAGACA TCGAGCTGTG CCTTGAAATT
ACTAACAACC AGGGATGGGA AACGAAGCCT GCTTTTGGAA AGACAACAAT GAGAGAGAGA
GAGAGAGGGA GAGAGACAAT GAGTGCCACA AACCTGGTAG TGCTCCGCCA ATGCGTCTGA
AATGTCACAT CCGAGTCTTG GGGCCTCTGT GAGAATGTCC AGAGTAATAC GTGTTTTGCG
AATAGTCCTC TTTCTTGAGG ACTGGATACC TACGATACCC TTTTTGAGTT GATGCGGTGC
TTTCGAAGTA TTATCTGGAG GATAGAAGAC GTCTAGGTAA CTACACAAAA GGCCTATACT
TTGGGGAGTA GCCCAACGAA AGGTAACTCC TACGGCCTCT TAGAGCCGTC ATAGATCCTA
CAGCCTCTTG GAGCCGTCAT AGATCACATC TGTGTAGACC GACATTCTAT GAATAATCAT
CTCATCATGG CCACATACTA CTACATACGT GTCTCTGCCT ACCTGACATG TAGCAGTGGC
CAAGACACCA AGGCCCCAGC ATCAAGCCTC CCTACCTATC CCTTCCATTG TACAGCGGCA
GAGAGATTGC GATGAGCCCT CTCCCTACCT ACAGACGGCT GACAATGTCC GTATACCACC
AGCCAACGTG ATGAAAACAA GGACATGAGG AACAGCCTGC GAGAGCTGGA AGATGAAGAG
GGCCAGAAAA AAAAGTATAA AGAAGACCTC GATTCCCGCC ATCCAACAAT CTTTTCCATC
CTCATCAGCA CACTCATCTA CAACCATCAC CACATTCACT CAACTCCTCT TTCTCAACTC
TCCAAACACA AACATTCTTT GTTGAATACC AACCATCACC ACCTTTCAAG ATGCAGTTCT
TCGCCGTCGC CCTCTTCGCC ACCAGCGCCC TGGCTGCTGT CTGCCCTACC GGCCTCTTCT
CCAACCCTCT GTGCTGTGCC ACCAACGTCC TCGACCTCAT TGGCGTTGAC TGCAAGACCC
GTATGTTGAA TTCCAATCTC TGGGCATCCT GACATTGGAC GATACAGTTG ACTTACACGA
TGCTTTACAG CTACCATCGC CGTCGACACT GGCGCCATCT TCCAGGCTCA CTGTGCCAGC
AAGGGCTCCA AGCCTCTTTG CTGCGTTGCT CCCGTGGTAA GTAGTGCTCG CAATGGCAAA
GAAGTAAAAA GACATTTGGG CCTGGGATCG CTAACTCTTG ATATCAAGGC CGACCAGGCT
CTCCTGTGCC AGAAGGCCAT CGGCACCTTC TAAAGCAATG GCTTGCTTTA CTGCCGGCAG
TCTTTGAGAA CTCTGGGCTC ACAAAAGACG ACTTGCATGT ATCATGGGGG CTCGCAAATG
GGAGGATTTG GAGGGGATTG AGGCTGGGTT TGGCCTATTA GAGGATTGCA TAATGGAAGA
TTTGCGAGCA GGACATAGAC GTATCTAGAG TTCTAGTCAA TACATTATTG AAAAGTTGGA
GTATACCTAT CGCTGGCACT GGTATCTTGA AGATATCTTC TCTTCTTGTG AGGTTATGTA
TGGCAATCAG TCGAAATCTA TTTGAAGACA GAGCTCAAGC TTCAAACATT CACCTGNGAA
TTGACCATTT TGTTTCGATG GTTGCAGTTG GTGGGTGTCA CTTCTGCAAT CATGTACGAG
CACAAGTATA GCAGTATTCC ATCTGATCTG CATCTGGGTA AATGTCGCCA CTCTACCTAG
GTACCCAATA AATACCGAAT TGGTCAGCTC TCGGGTGACA AACCGGCCCG CTTTTCGACC
GTGCTCTGTC CAATTCTAGG CTTGTCAATG GTTCCTGACT GTGATAAACC TTGGAGCTAN
CATAACTTAC CTTACAATAA ATCCAACTGC CGGCACTTGC TTCCCTTCAC CCAACCACTC
GCAAACATCA CGCAACCTGT CTCGATCCCC TGTCCGAAAT CTGCTTGGCA ACGTATCATC
ACAAATCATA CACACAGACA AAAAGGAGCC AAAGCAGCAA TGGCAAGACA CCGAGGCCGG
CAGCGCGCCC GTCGCCGTTT TTAAAAAGCG AAGCGCAAAG GGCAAAGCCA ACCTGCGCAA
ACGAACAACG AAGCCTTCCC CCCGCCGCGA GCGACAGCGA CAGCGACAGC GACTTTTCCT
CGTCGGAAGA CGAAGCCGGG CACAGAGTCA AGAGGCGCAA GAGGACGGCC GTCGTCACCG
CCGCCGCGGA GGGGCGCCGC GCCCAGCAAC CGGGACGACG GCGGCGGCGC AACAGCCGCC
TTCACGGCCA ACAGAAGCGT CCCGATTGCT GACAGCAACG ACGCGACCAA GCACAGCAAC
TGGTACGACG AGGACGCAAA GGACGCGCTC TCGGCAAAGA ACCTCCTCGG ATCTTCGAGA
GCGTCCAAGG ACGCGCAGCC AGACGGCACG TACAAGGGCC TGGCGAACCA GACGTCCTTT
ATACAAAAGA ATCCGGATGC GCCCCGGAAG ACAGTTGGGC CCGTCAAGGC GCCTACCAAC
ATCCGCACCG TCACCATTAC AGATTATGCC CCGGACACGT GTAAAGAGTG AGTTTGCATC
AATAGCCAGA ATCCCCCCCC CCGATACCGT ACATTGAGCA TATGCTGACT CGTCATAATC
TTTCTAGTTA TCGCATAACC GGCTATATAA GTACTCCCCT TTTCCATGAT TATTCCAGTC
GCGTACTGAC ATTTCTAGGA GCCTTTACTG TGGTTTTGGC GACAATTGCA AGTATCTTCA
CGCGAGAGAA GACCTCAAGG CAGGCTGGCA GCTGGATCAA GAGTGGGAAA AGGTCACCAA
GGGCAAGAAG AACCTGGGGG GAACGGTAGT GGCCAGCGCG AACCGGAACA AGGCCAAGGT
```

Fig. 2A

```
GGACGAGGGC GACGACGACG ACGACGAAGA GGCGATGCTC GAGAACATTC CGTTTGCCTG
CATCATCTGC AGGGAATCGT ACAAGGAGCC GATTGTGACG AGGTGCGGGC ACTACTTTTG
CCTGCCGTGC GCTCTGCAGC GGTACAAGAA GGATCCGACG TGTGCGGCGT GTGGCTCGGG
CACGAATGGC GTGTTTAATT CGGCGACGAG GTTGAAGAAG CTGCTGGAGA AGAAGAGGGA
GAGGGCGGCC AGGAGGAGAC AGGAGGCGAT AGAGAGGGGC GAGGAAGTCA GTGATGAAGA
GGAGGAGGAG GAGGAGGACT GATGATGATG GGGCNAGATG ACGATGCAGG TCGACTCTAG
AGATCCCCGG TACCGAGCTC GAATTCATCG ATGATATCAG ATCCC
                                     EcoRV
```

Fig. 2B

SEQUENCE LISTING

```
<160> NUMBER OF SEQ ID NOS: 9

<210> SEQ ID NO 1
<211> LENGTH: 2868
<212> TYPE: DNA
<213> ORGANISM: Trichoderma reesei
<220> FEATURE:
<221> NAME/KEY: gene
<222> LOCATION: (1523)..(1950)
<223> OTHER INFORMATION: hfb1

<400> SEQUENCE: 1
tttgtatggc tggatctcga aaggcccttg tcatcgccaa gcgtggctaa tatcgaatga      60
gggacaccga gttgcatatc tcctgatcat tcaaacgaca agtgtgaggt aggcaatcct     120
cgtatcccat tgctgggctg aaagcttcac acgtatcgca taagcgtctc caaccagtgc     180
ttaggtgacc cttaaggata cttacagtaa gactgtatta agtcagtcac tctttcactc     240
gggctttgaa tacgatcctc aatactcccg ataacagtaa gaggatgata cagcctgcag     300
ttggcaaatg taagcgtaat taaactcagc tgaacggccc ttgttgaaag tctctctcga     360
tcaaagcaaa gctatccaca gacaagggtt aagcaggctc actcttccta cgccttggat     420
atgcagcttg gccagcatcg cgcatggcca atgatgcacc cttcacggcc caacggatct     480
```

-continued

```
cccgttaaac tccctgtaa cttggcatca ctcatctgtg atcccaacag actgagttgg      540
gggctgcggc tggcggatgt cggagcaaag gatcacttca agagcccaga tccgttggt      600
ccattgccaa tggatctaga ttcggcacct tgatctcgat cactgagaca tggtgagttg     660
cccggacgca ccacaactcc ccctgtgtca ttgagtcccc atatgcgtct tctcagcgtg     720
caactctgag acggattagt cctcacgatg aaattaactt ccagcttaag ttcgtagcct     780
tgaatgagtg aagaaatttc aaaaacaaac tgagtagagg tcttgagcag ctggggtggt     840
acgcccctcc tcgactcttg ggacatcgta cggcagagaa tcaacggatt cacacctttg     900
ggtcgagatg agctgatctc gacagatacg tgcttcacca cagctgcagc taccttttgcc    960
caaccattgc gttccaggat cttgatctac atcaccgcag cacccgagcc aggacggaga    1020
gaacaatccg gccacagagc agcaccgcct tccaactctg ctcctggcaa cgtcacacaa    1080
cctgatatta gatatccacc tgggtgattg ccattgcaga gaggtggcag ttggtgatac    1140
cgactggcca tgcaagacgc ggccgggcta gctgaaatgt ccccgagagg acaattggga    1200
gcgtctatga cggcgtggag acgacgggaa aggactcagc cgtcatgttg tgttgccaat    1260
ttgagattgt tgaccgggaa aggggggacg aagaggatgg ctgggtgagg tggtattggg    1320
aggatgcatc attcgactca gtgagcgatg tagagctcca agaatataaa tatcccttct    1380
ctgtcttctc aaaatctcct tccatcttgt ccttcatcag caccagagcc agcctgaaca    1440
cctccagtca acttccctta ccagtacatc tgaatcaaca tccattcttt gaaatctcac    1500
cacaaccacc atcttcttca aaatgaagtt cttcgccatc gccgctctct ttgccgccgc    1560
tgccgttgcc cagcctctcg aggaccgcag caacggcaac ggcaatgttt gccctcccgg    1620
cctcttcagc aaccccagt gctgtgccac ccaagtcctt ggcctcatcg gccttgactg      1680
caaagtccgt aagttgagcc ataacataag aatcctcttg acggaaatat gccttctcac    1740
tcctttaccc ctgaacagcc tcccagaacg tttacgacgg caccgacttc cgcaacgtct    1800
gcgccaaaac cggcgcccag cctctctgct gcgtggcccc cgttgtaagt tgatgcccca    1860
gctcaagctc cagtctttgg caaacccatt ctgacaccca gactgcaggc cggccaggct    1920
cttctgtgcc agaccgccgt cggtgcttga gatgcccgcc cggggtcaag gtgtgccgt     1980
gagaaagccc acaaagtgtt gatgaggacc atttccggta ctgggaaagt tggctccacg    2040
tgtttgggca ggtttgggca agttgtgtag atattccatt cgtacgccat tcttattctc    2100
caatatttca gtacactttt cttcataaat caaaaagact gctattctct ttgtgacatg    2160
ccggaaggga acaattgctc ttggtctctg ttatttgcaa gtaggagtgg agattcgcc     2220
ttagagaaag tagagaagct gtgcttgacc gtggtgtgac tcgacgagga tggactgaga    2280
gtgttaggat taggtcgaac gttgaagtgt atacaggatc gtctggcaac ccacggatcc    2340
tatgacttga tgcaatggtg aagatgaatg acagtgtaag aggaaaagga aatgtccgcc    2400
ttcagctgat atccacgcca atgatacagc gatatacctc caatatctgt gggaacgaga    2460
catgacatat ttgtgggaac aacttcaaac agcgagccaa gacctcaata tgcacatcca    2520
aagccaaaca ttggcaagac gagagacagt cacattgtcg tcgaaagatg gcatcgtacc    2580
caaatcatca gctctcatta tcgcctaaac cacagattgt tgccgtcccc ccaactccaa    2640
aacgttacta caaaagacat gggcgaatgc aaagacctga agcaaacccc tttttgcgac    2700
tcaattccct ccttttgtcct cggaatgatg atccttcacc aagtaaaaga aaaagaagat    2760
tgagataata catgaaaagc acaacggaaa cgaaagaacc aggaaaagaa taaatctatc    2820
acgcaccttg tccccacact aaaagcaaca gggggggtaa aatgaaat               2868
```

<210> SEQ ID NO 2
<211> LENGTH: 3585
<212> TYPE: DNA
<213> ORGANISM: Trichoderma reesei
<220> FEATURE:
<221> NAME/KEY: gene
<222> LOCATION: (1191)..(1593)
<223> OTHER INFORMATION: hfb2
<220> FEATURE:
<221> NAME/KEY: unknown
<222> LOCATION: (1917)..(1917)
<223> OTHER INFORMATION: n = a, c, t, g, unknown, or other
<220> FEATURE:
<221> NAME/KEY: unknown
<222> LOCATION: (2160)..(2160)
<223> OTHER INFORMATION: n = a, c, t, g, unknown, or other
<220> FEATURE:
<221> NAME/KEY: unknown
<222> LOCATION: (3515)..(3515)
<223> OTHER INFORMATION: n = a, c, t, g, unknown, or other

<400> SEQUENCE: 2

| | | | | | |
|---|---|---|---|---|---|
| ctcgagcagc | tgaagcttgc | atgcctgcat | cctttgtgag | cgactgcatc | cattttgcac | 60 |
| acactgccgt | cgacgtctct | cttccgacct | tggccagctg | acaagcaac | acaccaatga | 120 |
| cgctttgtat | tattagagta | tatgcaagtc | tcaggactat | cgactcaact | ctacccaccg | 180 |
| aggacgatcg | cggcacgata | cgccctcgtt | ctcattggcc | aagcagacc | aactgccct | 240 |
| ggagcaagat | tcagcccaag | ggagatggac | ggcagggcac | gccagggccc | caccaccaag | 300 |
| ccactccctt | tggccaaatc | agcttgcatg | tcaagagaca | tcgagctgtg | ccttgaaatt | 360 |
| actaacaacc | agggatggga | aacgaagcct | gcttttggaa | agacaacaat | gagagagaga | 420 |
| gagagaggga | gagagacaat | gagtgccaca | aacctgtag | tgctccgcca | atgcgtctga | 480 |
| aatgtcacat | ccgagtcttg | gggcctctgt | gagaatgtcc | agagtaatac | gtgttttgcg | 540 |
| aatagtcctc | tttcttgagg | actggatacc | tacgatacc | ttttgagtt | gatgcggtgc | 600 |
| ttcgaagta | ttatctggag | gatagaagac | gtctaggtaa | ctacacaaaa | ggcctatact | 660 |
| tggggagta | gcccaacgaa | aggtaactcc | tacggcctct | tagagccgtc | atagatccta | 720 |
| cagcctcttg | gagccgtcat | agatcacatc | tgtgtagacc | gacattctat | gaataatcat | 780 |
| ctcatcatgg | ccacatacta | ctacatacgt | gtctctgcct | acctgacatg | tagcagtggc | 840 |
| caagacacca | aggccccagc | atcaagcctc | cctacctatc | ccttccattg | tacagcggca | 900 |
| gagagattgc | gatgagccct | ctccctacct | acagacggct | gacaatgtcc | gtataccacc | 960 |
| agccaacgtg | atgaaaacaa | ggacatgagg | aacagcctgc | gagagctgga | agatgaagag | 1020 |
| ggccagaaaa | aaaagtataa | agaagacctc | gattcccgcc | atccaacaat | cttttccatc | 1080 |
| ctcatcagca | cactcatcta | caaccatcac | cacattcact | caactcctct | ttctcaactc | 1140 |
| tccaaacaca | aacattcttt | gttgaatacc | aaccatcacc | acctttcaag | atgcagttct | 1200 |
| tcgccgtcgc | cctcttcgcc | accagcgccc | tggctgctgt | ctgccctacc | ggcctcttct | 1260 |
| ccaaccctct | gtgctgtgcc | accaacgtcc | tcgacctcat | tggcgttgac | tgcaagaccc | 1320 |
| gtatgttgaa | ttccaatctc | tgggcatcct | gacattggac | gatacagttg | acttacacga | 1380 |
| tgctttacag | ctaccatcgc | cgtcgacact | ggcgccatct | tccaggctca | ctgtgccagc | 1440 |
| aagggctcca | agcctctttg | ctgcgttgct | cccgtggtaa | gtagtgctcg | caatggcaaa | 1500 |
| gaagtaaaaa | gacatttggg | cctgggatcg | ctaactcttg | atatcaaggc | cgaccaggct | 1560 |
| ctcctgtgcc | agaaggccat | cggcaccttc | taaagcaatg | gcttgcttta | ctgccggcag | 1620 |

-continued

```
tctttgagaa ctctgggctc acaaaagacg acttgcatgt atcatggggg ctcgcaaatg      1680
ggaggatttg gagggattg aggctgggtt tggcctatta gaggattgca taatggaaga       1740
tttgcgagca ggacatagac gtatctagag ttctagtcaa tacattattg aaaagttgga     1800
gtatacctat cgctggcact ggtatcttga agatatcttc tcttcttgtg aggttatgta     1860
tggcaatcag tcgaaatcta tttgaagaca gagctcaagc ttcaaacatt cacctgngaa     1920
ttgaccattt tgtttcgatg gttgcagttg gtgggtgtca cttctgcaat catgtacgag     1980
cacaagtata gcagtattcc atctgatctg catctgggta aatgtcgcca ctctacctag     2040
gtacccaata aataccgaat tggtcagctc tcgggtgaca aaccggcccg cttttcgacc     2100
gtgctctgtc caattctagg cttgtcaatg gttcctgact gtgataaacc ttggagctan     2160
cataacttac cttacaataa atccaactgc cggcacttgc ttcccttcac ccaaccactc     2220
gcaaacatca cgcaacctgt ctcgatcccc tgtccgaaat ctgcttggca acgtatcatc     2280
acaaatcata cacacagaca aaaggagcc aaagcagcaa tggcaagaca ccgaggccgg      2340
cagcgcgccc gtcgccgttt taaaaagcg aagcgcaaag ggcaaagcca acctgcgcaa      2400
acgaacaacg aagccttccc cccgccgcga gcgacagcga cagcgacagc gacttttcct    2460
cgtcggaaga cgaagccggg cacagagtca agaggcgcaa gaggacggcc gtcgtcaccg    2520
ccgccgcgga ggggcgccgc gcccagcaac cgggacgacg gcgcggcgc aacagccgcc     2580 ttcacggcca acagaagcgt cccgattgct gacagcaacg acgcgaccaa gcacagcaac    2640
tggtacgacg aggacgcaaa ggacgcgctc tcggcaaaga acctcctcgg atcttcgaga    2700
gcgtccaagg acgcgcagcc agacggcacg tacaagggcc tggcgaacca gacgtccttt    2760
atacaaaaga atccggatgc gccccggaag acagttgggc ccgtcaaggc gcctaccaac    2820
atccgcaccg tcaccattac agattatgcc ccggacacgt gtaaagagtg agtttgcatc    2880
aatagccaga atccccccccc ccgataccgt acattgagca tatgctgact cgtcataatc    2940
tttctagtta tcgcataacc ggctatataa gtactcccct tttccatgat tattccagtc    3000
gcgtactgac atttctagga gcctttactg tggttttggc gacaattgca agtatcttca    3060
cgcgagagaa gacctcaagg caggctggca gctggatcaa gagtgggaaa aggtcaccaa    3120
gggcaagaag aacctggggg gaacggtagt ggccagcgcg aaccggaaca aggccaaggt    3180
ggacgagggc gacgacgacg acgacgaaga ggcgatgctc gagaacattc cgtttgcctg    3240
catcatctgc agggaatcgt acaaggagcc gattgtgacg aggtgcgggc actacttttg    3300
cctgccgtgc gctctgcagc ggtacaagaa ggatccgacg tgtgcggcgt gtggctcggg    3360
cacgaatggc gtgtttaatt cggcgacgag gttgaagaag ctgctggaga agaagaggga   3420
gagggcggcc aggaggagac aggaggcgat agagaggggc gaggaagtca gtgatgaaga   3480
ggaggaggag gaggaggact gatgatgatg gggcnagatg acgatgcagg tcgactctag    3540
agatccccgg taccgagctc gaattcatcg atgatatcag atccc                    3585
```

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: 5' primer

<400> SEQUENCE: 3

```
actacacgga ggagctcgac gacttcgagc agcccgagct gcacgcagag caacggcaac      60
ggc                                                                    63
```

-continued

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: 3'primer

<400> SEQUENCE: 4
tcgtacggat cctcaagcac cgacggcggt                                        30

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: linker

<400> SEQUENCE: 5

Pro Gly Ala Ser Thr Ser Thr Gly Met Gly Pro Gly Gly
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: linker

<400> SEQUENCE: 6

Gly Thr Leu Val Pro Arg Gly Pro Ala Glu Val Asn Leu Val
1               5                   10

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: 5'primer

<400> SEQUENCE: 7
gaattcggta ccctcgtccc tcgcggtccc gccgaagtga acctggtg                    48

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: 3'primer

<400> SEQUENCE: 8
tgaattccat atgctaaccc cgtttcatct ccag                                   34

<210> SEQ ID NO 9
<211> LENGTH: 157
<212> TYPE: PRT
<213> ORGANISM: Artificial Sequence
<220> FEATURE:
<223> OTHER INFORMATION: Hydrophobin protein derived from fungi
<220> FEATURE:
<221> NAME/KEY: misc_feature
<222> LOCATION: (1)..(38)
<223> OTHER INFORMATION: Xaa can be any naturally occurring amino acid
      and at least 2 and up to 38 amino acids can either be present or
      absent
<220> FEATURE:
<221> NAME/KEY: misc_feature
<222> LOCATION: (40)..(48)
```

```
<223> OTHER INFORMATION: Xaa can be any naturally occurring amino acid
      and at least 5 and up to 9 amino acids can either be present or
      absent
<220> FEATURE:
<221> NAME/KEY: misc_feature
<222> LOCATION: (51)..(89)
<223> OTHER INFORMATION: Xaa can be any naturally occurring amino acid
      and at least 11 and up to 39 amino acids can either be present or
      absent
<220> FEATURE:
<221> NAME/KEY: misc_feature
<222> LOCATION: (91)..(113)
<223> OTHER INFORMATION: Xaa can be any naturally occurring amino acid
      and at least 8 and up to 23 amino acids can either be present or
      absent
<220> FEATURE:
<221> NAME/KEY: misc_feature
<222> LOCATION: (115)..(123)
<223> OTHER INFORMATION: Xaa can be any naturally occurring amino acid
      and at least 5 and up to 9 amino acids can either be present or
      absent
<220> FEATURE:
<221> NAME/KEY: misc_feature
<222> LOCATION: (126)..(143)
<223> OTHER INFORMATION: Xaa can be any naturally occurring amino acid
      and at least 6 and up to 18 amino acids can either be present or
      absent
<220> FEATURE:
<221> NAME/KEY: misc_feature
<222> LOCATION: (145)..(157)
<223> OTHER INFORMATION: Xaa can be any naturally occurring amino acid
      and at least 2 and up to 13 amino acids can either be present or
      absent

<400> SEQUENCE: 9

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Cys Xaa Xaa Xaa Xaa Xaa Xaa Xaa Xaa
                35                  40                  45

Cys Cys Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Cys Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Cys Xaa Xaa Xaa Xaa Xaa Xaa Xaa Xaa Cys Cys Xaa Xaa Xaa
    115                 120                 125

Xaa Xaa Xaa Xaa Xaa Xaa Xaa Xaa Xaa Xaa Xaa Xaa Xaa Xaa Cys
    130                 135                 140

Xaa Xaa Xaa Xaa Xaa Xaa Xaa Xaa Xaa Xaa Xaa Xaa Xaa
145                 150                 155
```

METHOD FOR DECREASING THE FOAM FORMATION DURING CULTIVATION OF A MICROORGANISM

BACKGROUND OF THE INVENTION

This invention relates to a novel method for decreasing the foam formation during the cultivation of *Trichoderma* production host, to a method for producing a product by cultivating a microorganism and to a novel production host strain with decreased foam formation during cultivation. Furthermore this invention relates to a process for producing an enhanced amount of a product of interest according to the method for decreasing the foam formation during cultivation of a *Trichoderma* production host.

When microorganisms are cultured in liquid growth medium in laboratory vessels or in small or large scale bioreactors, a common feature is foaming. In particular, this is a problem in aerated bioreactor or, as they are usually called, fermentor cultivations. Biochemically, the term "fermentation" refers to the process of ethanol production in yeasts by anaerobic metabolism. Modern aseptic submerged "fermentation" of individual selected microbes is used for production of cell mass, proteins such as enzymes and antibodies, and other metabolites such as antibiotics, amino acids and organic acids. The main microorganisms used in industry in fermentation are fungi, especially filamentous fungi and yeast, especially filamentous fungi and yeast, and bacteria, such as *Bacillus* spp., *Escherichia coli* and *Streptomyces* spp.

Typically only 70-80% of the fermentation vessel volume is filled with liquid and a gas space occupies the top portion of the tank. The combined action of aeration and agitation of the liquid promotes the formation of a foam on the liquid surface and normally all aerated fermentation broths foam, which is why a large gas space is required. Foam impedes gas mass transfer from the broth to the head space, forcing foam out of the vessel and contaminating the system when collapsed foam re-enters the fermentor. This means that some foam control method should always be included in fermentations. The two methods most commonly used for commercial fermentations are mechanical foam breakers and/or addition of antifoam agents.

A mechanical foam breaker is a high-speed impeller designed very much like a centrifugal pulp impeller. Foam is drawn into the impeller, where it is collapsed by strong mechanical forces. This is not suitable for delicate organisms. The impeller must be mounted on its own shaft and driven independently of the main agitator. This requires a separate agitator seal, which is a potential source of contamination and other problems. Mechanical foam breakers also represent a conciderable capital outlay.

Chemical antifoam agents collapse foams by altering their surface tension characteristics. Sterile antifoam agent is usually pumped into the fermentor automatically from an addition vessel. Addition of antifoam agent results in a possible contamination risk because the polymeric water-free liquid agents are difficult to sterilize. The choice of antifoam agent cannot be made only on the basis of its compatibility with the fermentation, but also with product recovery, concentration and purification in downstream processing. For example particularly silicon-based antifoam agents may decrease dramatically the permeate flux through certain types of membrane filters even at very low concentrations. Hydrophobic antifoam agents bind to the hydrophobic ultrafiltration membranes, lowering the permeate flux, and may change dramatically the apparent molecular weight cut-off of the membranes.

The first antifoam agents to be used in fermentation were silicone-based fluids. More recently, oil-based antifoam agents with a chemical structure consisting of polymers of e.g. ethylene and propylene oxides with esters of long-chain fatty acids have commonly been used. All antifoam agents have a "cloud point", above which they are essentially insoluble in water. The functional properties of the antifoam agents operate at temperatures above the cloud point. Therefore the cloud point of the antifoam agent should be below the temperature of the fermentation. However, for example membrane filtration should be operated at temperatures below the cloud point, so that the antifoam agent will be water-soluble and therefore have minimal effect on the filtration procedure. Antifoam agents are available with very variable cloud points.

Most antifoam agents, because of their hydrophobic nature, are difficult to sterilise. They may also represent a considerable cost outlay. A good antifoam control system should also include an option to reduce automatically the air flow and the agitation speed when foaming overwhelms the system and the fermenter is in danger of being emptied. This is necessary to avoid damage to the drive system if the fermenter is emptied because of overfoaming.

Because of their function of disrupting air-filled bubbles both above and within the fermentation broth, antifoam agents considerably reduce the oxygen transfer rate. By contrast, detergents usually enhance oxygen transfer rates. When antifoam agents and detergents are present simultaneously, they exert compensating effects. Oxygen transfer rates depressed owing to the addition of antifoam agent result in decreased dissolved oxygen levels at a constant rate of agitation and aeration. Antifoam agents decrease the surface tension, resulting in reduced volumetric mass transfer coefficient ($k_L a$) values. This leads to a need for increased aeration and agitation, which in turn enhances foam formation and necessitates further addition of antifoam agent which further enhances the problems created by antifoam agent. The positive feedback effects of foaming and agitation/aeration represent a major problem in many commercial fermentation processes. A further practical disadvantage is reduced sensitivity and accelerated ageing of probes due to clogging by the polymer components of the antifoam agents.

Production media used in industrial fermentations often contain insoluble polymers. The presence of these insoluble medium components considerably aggravates the problem of foaming during fermentation. The foam produced during cultivation combines with unutilised solid particles from the medium to form a composite foam with strong physical properties and undesirably high persistence. This foam-solids conglomerate can remain attached to the sides of the vessel and to other steel structures in the fermenter headspace independently of support from below, and contact between the broth and foam layers is disestablished. Addition of antifoam agent to the fermentation is therefore not successful in degrading the secondary foam structure. Thus after establishment of contact between the upper foam layer and the tip of the antifoam probe, the subsequent automatic addition of antifoam agent does not disrupt the foam layer. In this case, addition of antifoam agent may, and frequently does, continue indefinitely until the addition vessel becomes empty. Despite continuing addition of antifoam agent, the conglomerate foam layer continues to rise in the fermenter headspace, eventually entering the exhaust line and blocking the outlet filter. This in turn prevents the passage of air through the broth and the dissolved oxygen decreases to zero, with disastrous effects on the production process. This whole cycle may occur in a short period of only 1-2 hours.

Oxygen transfer rate is affected by the microbial species, its morphology and concentration. Species with more complex morphology (pellets versus filaments, pellets do not have significantly higher oxygen demand and uptake but clearly higher maximum oxygen transfer rate) lead to lower oxygen transfer rates. Increased viscosity due to the high mycelial concentrations (pseudoplastic moulds) concentration leads to reduced oxygen transfer rates.

Mycelial morphology also affects the process productivity and kinetics. In some cases the small pellets are optimal for the production of desired product whereas in other cases filamentous growth has been found to be optimal. The morphology also affects the downstream prossessing and filtration properties of the culture liquid as larger particles are easier to separate e.g. in vacuum drum filtration. Growth in the form of pellets usually leads to an interstitial culture fluid with greater clarity and lower viscosity than in the case of diffuse mycelial growth.

Because of the several problems caused by foam formation during fermentation there is a high demand for new ways to hinder or cut down the foam formation.

There are some prior art publications which relate to the production of surfactins in *Bacillus* strain bacteria. EP 576 050 describes the isolation and characterization of the sfp gene in *Bacillus subtilis*, which codes for a protein for producing the lipopeptide surfactin. Surfactin is a specific protein, where the lipide part is covalently bound to the protein part. Foaming properties of surfactin from *B. subtilis* are discussed in Razafindralambo et al. (1996) and surfactin negative phenotype of *B. subtilis* in D' souza et al. (1993). WO 98/22598 suggested a modification to a *Bacillus* cell to produce a lower level of surfactin. The modification was reported to result in reduced foaming. However, these publications were restricted to the surfactins of *Bacillus*.

WO 96/41882 suggested the production of hydrofobins from edible fungi for food industry. The publication describes the overexpression of hydrophobins and does not discuss the foaming problem.

SUMMARY

It is an aim of the present invention to eliminate the problems associated with the prior art and to provide a solution to the problems caused by foaming during cultivation of various kinds of microorganisms. The present invention provides a totally new way to solve the foaming problem, which results in minimal or no need to use antifoam agents.

The present invention provides in particular a method to eliminate or diminish the production of proteins, polypeptides or peptides associated with foam formation during cultivation of microorganisms. The method comprises genetic modification of desired microorganisms not to produce proteins, polypeptides or peptides associated with foam formation, or to produce them only in essentially reduced amounts. Such proteins, polypeptides or peptides are recoverable from foam produced in cultivation of the microorganisms. The microorganisms are selected from the group comprising yeast, fungi, bacteria, plant cells and animal cells. Preferably they are production strains used in producing a product of interest, such as desired proteins, polypeptides, metabolites or biomass. Typically such strains are genetically modified to produce these products in an efficient way.

One object of the present invention is a method for decreasing the level of foam formation during cultivation of a microorganism, comprising the steps of
modifying the microorganism in such a way that the micoorganism does not produce an essential amount of proteins, polypeptides or peptides associated with foam formation during cultivation of the microorganism; and
cultivating the microorganism under suitable culture conditions.

More specifically, the method is mainly characterized by what is stated in the characterizing part of claim 1.

The "modification" of the microorganism is preferably "genetic modification", which means that at least one of the DNA sequences, or parts of it, encoding proteins, polypeptides or peptides associated with foam formation is modified not to be expressed and/or secreted. The genetic modification comprises various methods directed to the regulatory region of the DNA sequence encoding the desired protein, polypeptide or peptide or various methods with which the DNA sequence can be inactivated, such as mutagenesis or deletion, or the genetic modification comprises various methods directed to DNA sequences encoding proteins regulating the production of proteins, polypeptides or peptides associated with foam formation. The genetic modification according to this invention is preferably made by inactivating the desired DNA sequence or sequences of the proteins, polypeptides or peptides associated with foam formation. More preferably, the genetic modification is made by deleting the desired DNA sequence or sequences. This is because deletion is the most powerful technique to diminish the effect of the proteins, polypeptides or peptides associated with foam formation.

Molecules associated with foam formation during cultivation are various proteins, polypeptides or peptides recoverable from the foam formed in cultivation of the microorganism or their regulatory proteins. Such molecules comprise proteins, polypeptides or peptides, which regulate the production of foam-forming proteins, polypeptides or peptides which are responsible for foam formation. Preferably they are proteins, polypeptides or peptides, which are foam-forming i.e., which are responsible for foam formation. Such proteins, polypeptides and peptides comprise hydrophobic or amphipathic proteins, polypeptides or peptides, hydrophobins, or amphipathic surface active molecules. Preferably the proteins, polypeptides or peptides associated with foam formation are hydrophobins. Hydrophobins are among the most abundantly produced proteins of fungi. All fungi studied hitherto for the presence of hydrophobins have been shown to produce one or more of them.

Because many microbial production hosts are known to produce foam-forming proteins, polypeptides or peptides during cultivation, the present invention can be applied to solve the foaming problem in the cultivation of various different kinds of microorganisms.

According to a one preferred embodiment of this invention the microorganism is a fungus. More preferably, the fungus is *Trichoderma*.

According to a preferred embodiment of this invention the proteins, polypeptides or peptides, the production of which is eliminated or diminished, are hydrophobins from *Trichoderma*.

According to a highly preferred embodiment of this invention the hydrophobins are hydrophobin I (HFBI) or hydrophobin II (HFBII). The invention comprises that a *Trichoderma* strain is genetically modified not to produce essential amounts of HFBI and/or HFBII. Preferably the DNA sequences encoding hydrophobin I (HFBI) or hydrophobin II (HFBII) or both are inactivated in the *Trichoderma* strain.

According to another preferred embodiment of this invention the microorganism belongs to bacteria. The host strain may be any bacterial host producing proteins, polypeptides or peptides associated with foam formation during cultivation. Preferably the host strain is *E. coli*, or belongs to the genus *Bacillus* or *Streptomyces*.

Another object of the present invention is a new production host strain, which is genetically modified not to produce essential amounts of one or more of the proteins, polypeptides or peptides associated with foam formation when the non-modified production host strain is cultivated.

More specifically, the production host strain is mainly characterized by what is stated in the characterizing part of claim 15.

One further object of the present invention is a product produced by the microorganism cultivated by the method of this invention as stated in the characterizing part of claim 12. The product can be any natural or recombinant protein, peptide, metabolite, antibiotic, fusion protein or even the cells themselves. The product is preferably a recombinant product.

In this invention has also been found that a production host modified not to produce at least one hydrophobic or amphipathic protein, polypeptide or peptide is capable of producing an enhanced amount of a product of interest. This feature may also be seen in cultivations, where there is no essential reduction of foam formation during cultivation.

One still further objects of the present invention is therefore a production host strain genetically modified not to produce an essential amount of at least one of amphipathic or hydrophobic proteins, polypeptides or peptides as defined in the characterizing part of claim 24.

Furthermore one object of the present invention is a process for producing an enhanced amount of a product of interest as stated in the characterizing part of claim 34.

The present invention results in various advantages. When little or essentially no foam is formed during the cultivation of a microorganism, no or only low levels of antifoaming agents are needed. This results in significatly easier downstream processing.

The cultivation of a microorganism modified according to this invention results in no or substantially reduced overfoaming. Hence, the yield is higher, when the product losses are smaller.

One clear advantage is also that the contamination risk is significantly lower when there is no need to add antifoam agents, which are difficult to sterilize and because the growth medium does not come into contact with the surface or other potentially nonaseptic areas of the bioreactor system.

According to this invention there will be less attachment of the cultivation medium to the fermentor surfaces, electrodes, impeller etc. Thus the distribution of cell mass in the fermentor is more homogenous. In addition the malfunction of electrodes is decreased, which in turn improves the controllability of the fermentation.

As a result of this invention the overall productivity will be improved. One or several of the following parameters: product/protein secretion ratio, the specific productivity/protein ratio (protein/biomass) or productivity/fermentation ratio (more liquid in fermentor) will be higher compared to the ratios in cultivations which are not modified according to this invention.

Surprisingly the amount of soluble proteins, i.e amount of proteins secreted from the production host, is enhanced in cultivations. The amount of soluble proteins may be at least 1.2 times, preferably at least 2, more preferably at least 3, still more preferably at least 5, most preferably 10 times higher than the amount of proteins produced by a host not modified according to this invention. In this invention the remarkable finding has been made that by genetically modifying a microorganism host not to produce essential amounts of amphipathic or hydrophobic proteins, polypeptides or peptides, preferably hydrofobins, the production level of the host can be increased. Preferably, according to this invention the microorganism host should be modified not to produce at least one amphipathic or hydrophobic protein, polypeptide or peptide, preferably hydrophobin. The genetical modification disclosed in this invention can be used for improving the production levels of the modified microorganisms. The increased production of other proteins is shown in example 8.

Sometimes the decreased foam formation may remain unnoticed, depending on the aeration, media or other parameters, although the effect is evident in certain cultures. Also since production of large amounts of other proteins may cause foaming, the reducing effect of decreased production of hydrophobic or amphipathic proteins may be masked, and not clearly measurable, if in these strains the production of other proteins is increased.

One further advantage is that the productivity will be better due to altered morphology. By inactivation of one or more hydrophobin genes it is possible to control the morphology of the strain in between filamentous or pellet-forming growth.

The invention is of advantage particularly when cultivating microorganisms on a culture medium comprising insoluble components. Antifoam agents cannot degrade efficiently the composite foam formed from proteinaceous foam produced by the microbe metabolism and unutilized solid particles. According to this invention no or only diminished amount of foam is formed and hence no undegradable secondary structure foam is hampering the cultivation. The present invention is of advantage particularly when cultivating a production host in order to produce a product of interest, in particular a protein of interest.

BRIEF DESCRIPTION OF THE FIGURES

FIG. 1 shows the hfb1 genomic sequence (SEQ ID No 1) of 2868 bp, which contains protein encoding (and introns) and flanking sequences (not all of the subcloned flanking sequences are sequenced).hfb1 gene sequence is underlined-.MunI restriction sites used for cloning of the marker gene are in bold and underlined.

FIG. 2 shows hfb2 genomic sequence (SEQ ID No 2) of 3585 bp, which contains protein encoding (and introns) and flanking sequences. hfb2 gene sequence is underlined. BglI and EcoRV restriction sites used for cloning of the marker gene are in bold and underlined. Polylinker sequence of the cloning vector is in Italics and the restriction sites within the polylinker used for cloning purposes are underlined.

DETAILED DESCRIPTION OF THE INVENTION

Figure 3:
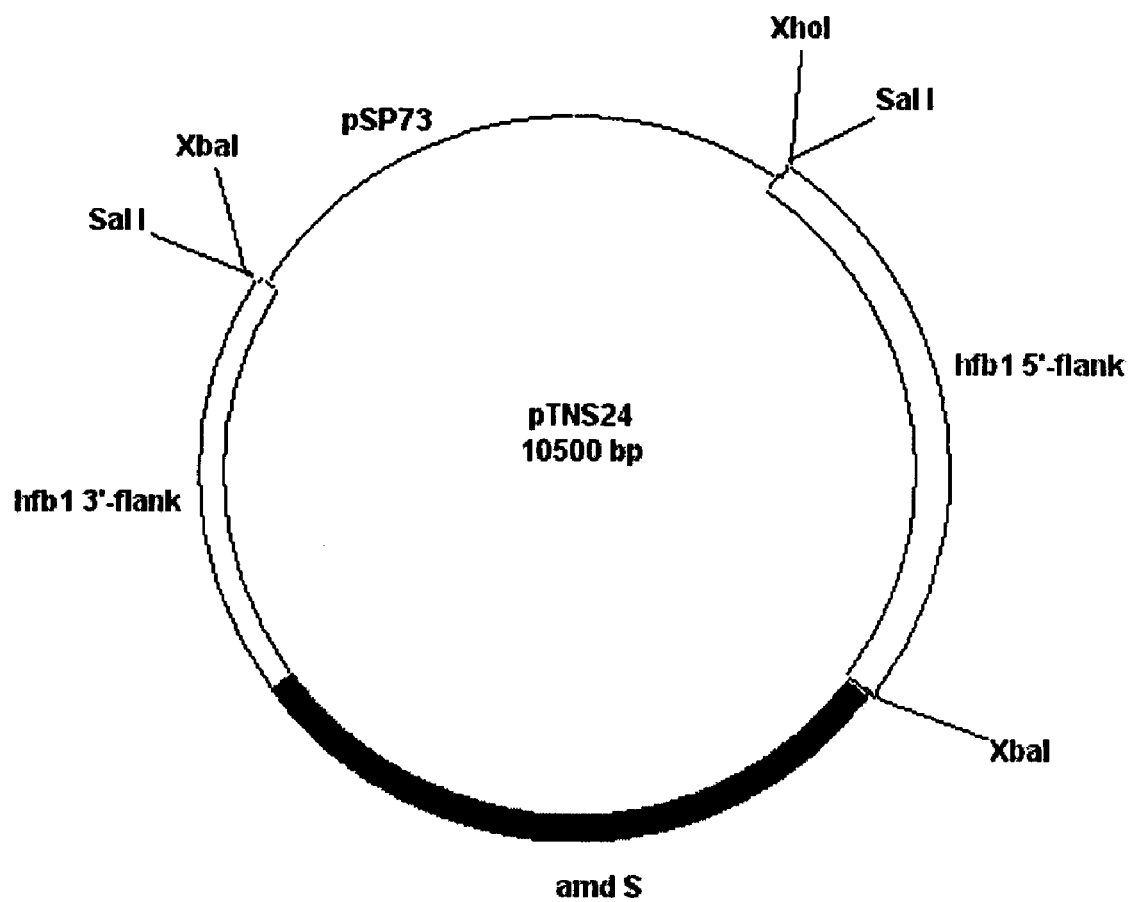
FIG. 3 depicts plasmid pTNS24

The term cultivation denotes here any methods used to grow microbial cells in a laboratory container or in large scale. The present invention is particularly useful to be applied to bioreactor cultivations, which are aerated and/or agitated.

The growth or cultivation medium should be chosen according to the microorganism in question. To achieve optimal growth of the microorganism and/or optimal production of the desired product, nutrients, aeration and pH conditions must be optimal for the microorganism. The cultivation medium may optionally be a medium which does not induce or which hinders the production of proteins or polypeptides, which are associated with foam formation during cultivation. The product of interest may be the cultivation medium with cells, it may be recovered from the cells or from the medium, preferably it may be recovered from the culture medium.

The term fermentation denotes here any bioreactor cultivations, preferably cultivations, in which agitation and/or aeration are used. The fermenter is preferably a normal fermentor, but the invention may be applied to airlift or other fermentor types.

The term microorganism denotes here bacteria, yeast, fungi, plant and animal cells. Preferably the invention is applied to fungi or bacteria, more preferably to fungi.

Fungal host strains of this invention comprise *Aspergillus* spp., *Trichoderma* spp., *Neurospora* spp., *Fusarium* spp., *Penicillium* spp., *Humicola* spp., *Tolypocladium geodes*, *Kluyveromyces* spp., *Pichia* spp., *Hansenula* spp., *Candida* spp., *Yarrowia* spp, *Schizosaccharomyces pombe*, *Saccharomyces* spp.

Bacterial host strains of this invention comprise *Bacillus* spp. *Zymomonas* spp. and Actinomycetales, such as *Streptomyces* spp., *Nocardia* spp. and *Escherichia coli*

A production host strain denotes here any microorganism, which is selected or genetically modified to produce efficiently a desired product and is useful for industrial application. The host strain is preferably a recombinant strain modified by gene technological means to efficiently produce a product of interest.

The term genetic modification comprises recombinant DNA technology or gene technology, cell fusion and hybridisation, mutagenesis, induced polyploidy, conjugation, transduction, transformation and injection of heritable material into a cell.

Genetic modification of a microorganism not to produce an essential amount of at least one of the proteins or peptides associated with foam formation during cultivation of the non-modified microorganism strain comprises that DNA sequences encoding at least one of the proteins, polypeptides or peptides associated with foam formation are modified by various genetical methods not to be expressed or secreted. Alternatively DNA sequences encoding regulatory proteins regulating the production of foam-forming proteins, polypeptides or peptides or the DNA sequences encoding foam-forming proteins, polypeptides or peptides are genetically modified. Genetic modification comprises furthermore that regulatory regions of the genes encoding proteins, polypeptides or peptides associated with foam formation are genetically modified. According to a preferred embodiment of this invention the DNA sequences encoding foam-forming proteins, polypeptides or peptides are made inactive. The inactivation may be made by any suitable conventional or molecular biology method well known in the art. The modification is preferably made by recombinant DNA techniques, such as by site directed mutagenesis or deletion. Most preferably the inactivation is made by deleting the DNA sequence encoding the chosen protein, polypeptide or peptide.

The above-mentioned methods can be used also to modify a microorganism not to produce amphipathic or hydrophobic proteins, polypeptides or peptides, preferably hydrophobins, in order to enhance the amount of production of a product of interest. These amphipathic or hydrophobic proteins, polypeptides or peptides are preferably found in the cell wall of the microorganism host.

Cultivation products may preferably include desired proteins, polypeptides, peptides, metabolites or cell mass.

The expression proteins, polypeptides or peptides associated with foam formation refers here to any molecule, which is associated with foam formation during cultivation of a microorganism and which is recoverable from the foam formed during cultivation of the microorganism. The group comprises foam-forming proteins, polypeptides or peptides and proteins, polypeptides or peptides regulating the production of foam-forming proteins or peptides. Preferably the group comprises hydrophobic or amphipathic proteins, polypeptides or peptides, hydrophobins or amphipathic surface active molecules and proteins. Preferably the proteins or peptides associated with foam formation are hydrofobins or hydrophobib-like molecules.

Examples of molecules responsible for foam formation during cultivation are hydrophobic, amphipathic proteins and peptides. Hydrophobins are secreted amphipathic proteins with interesting physico-chemical properties that have recently been discovered from filamentous fingi (Wessels, 1994; Wösten and Wessels, 1997; Kershaw and Talbot, 1998). They were first discribed at DNA level (Schuren and Wessels, 1990) and later identified as proteins that are active in the interaction between the fungal surface and the environment. Although the term "hydrophobin" had been used earlier to denote any hydrophobic material on the microbial surfaces, the term hydrophobin was used by Wessels to name these proteins (Wessels et al., 1991a,b). Hydrophobins are among the most abundantly produced proteins of fingi and all fingi studied hitherto have produced one or more hydrophobins. They can be recovered in varying amounts from e.g. the cell wall, conidia, fruiting bodies or culture medium.

One characteristic feature of these proteins is their moderate hydrophobicity. They are usually small proteins, approximately 70 to 160 amino acids, containing six to ten, usually eight cysteine residues in conserved pattern. The eight cysteine residues (Cys) have a conserved spacing: $X_{2-38}$-Cys-$X_{5-9}$-Cys-Cys-$X_{11-39}$-Cys-$X_{8-23}$-Cys-$X_{5-9}$-Cys-Cys $X_{6-18}$-Cys-$X_{2-13}$, in which X means any other amino acid. However, multimodular proteins with one or several hydrophobin domains and e.g. proline-rich or asparagine/ glycine repeats, or hydrophobins containing less than eight cysteine residues have also been characterized (Lora et al., 1994; Lora et al., 1995; Arntz and Tudzynski, 1997; de Vries et al. 1999).

Hydrophobins have been divided into two classes based on their hydropathy profiles and physico-chemical properties (Wessels, 1994). Class I hydrophobins form highly insoluble assemblages, whereas Class II hydrophobins assemblages are less stable and are soluble e.g. in 60% ethanol and 2% SDS. However most probably some hydrophobins exhibit characteristics between these two classes. Although more than 30 gene sequences for hydrophobins have been published (Wösten and Wessels, 1997), only few of the proteins have been isolated and studied. Today most protein data exists for the hydrophobins SC3 of *Schizophyllum commune* (Class I), cerato-ulmin of *Ophiostoma ulmi* and cryparin of *Cryponectria parasitica* (Class II). Other isolated hydrophobins include at least SC4 of *S. commune*, ABH1 and ABH2 of *Agaricus bisporus* and EAS of *Neurospora crassa*.

The most characteristic feature of hydrophobins is that they self-assemle at hydrophilic/hydrophobic interfaces. By self assembly at the interfaces between the hydrophilic cell wall and a hydrophobic environment (air, oil, soil), emergent structures are covered with an amphipathic membrane. The transition of hydrophilic to hydrophobic cell surface allows formation of aerial hyphae, facilitates dispersion of spores by wind, maintains open air channels within fruiting bodies, and mediates hyphal attachment and signaling of surface hydrophobicity. Hydrophobins make the areal hyphae water resistant and water repellant. Moreover they are involved in complex interhyphal interactions.

Hydrophobins do not only assemble at the cell wall/air or liquid interface but also at the interface between the hydrophilic cell wall and a hydrophobic solid. Hydrophobins firmly glue fungal hyphae and hydrophobic surfaces together (Wösten et al., 1994a). The adhesion of the hyphae to the solid surface is due to the amphipathic nature of the hydrophobin membrane, i.e. each side interacts with one of the two surfaces.

Hydrophobins also assemble at liquid-air interfaces. Several hydrophobins such as SC3 of *S. commune*, COH1 of *Coprinus cinereus*, ABH3 of *A. bisporus* and POH2 and POH3 of *Pleurotus ostreatus* are secreted into the culture medium (Wösten et al., 1999). Filamentous fungal species, such as *Aspergillus nidulans, A. niger, A. oryzae, Neurospora crassa* and *Penicillium chrysogenum* produce amphipathic proteins, most probably hydrophobins to the culture medium (de Vries et al., 1993, Wessels, 1997).

Hydrophobins are secreted as monomers, but when they encounter an air-water interface or an interface with hydrophobic surface, they aggregate to a larger polymeric complex. This thin layer formed is hydrophobic on one side and hydrophilic on the other. The SC3 assemblages, as well as those of cerato-ulmin and cryparin (Wessels, 1997), form on gas-liquid or oil-liquid interphases thus stabilizing air bubbles or oil droplets in water. The self-assembly of purified SC3 hydrophobin into an amphipathic layer occurs also on hydrophilic and hydrophobic surfaces (Wösten et al., 1993; Wösten et al., 1994b). This film is very strongly attached to the surface and not broken, for instance, by hot detergent. The hydrophobic side of the layer on hydrophilic surfaces shows properties similar to those of teflon (Wessels, 1994). Upon shaking SC3 hydrophobin-containing solutions, the protein monomers form 10 nm rodlet-like aggregates. These structures are similar to those found on surfaces of fungal aerial structures.

Several biosurfactants that decrease water surface tension are known in the literature (Wösten and Wessels, 1997). Surface activity of proteins is generally low but hydrophobins belong to surface-active molecules, their surfactant capacity being at least similar to traditional biosurfactants such as glycolipids, lipopeptides/lipoproteins, phospholipids, neutral lipids and fatty acids (Wösten and Wessels, 1997). In fact SC3 hydrophobin is the most potent biosurfactant known. It lowers the water surface tension to 24 $mJm^2$ at a concentration of 50 µg/ml. However in contrast to other biosurfactants, surface activity of hydrophobins is not dependent on a lipid molecule but apparently caused solely by the amino acid sequence. The glycan part of SC3 is mainly present in the hydrophilic part of the protein, probably contributing to the hydrophilicity of this part of the protein. However, most hydrophobins are not glycosylated and none of them is reported to be a lipoprotein. Furthermore, surface activity of hydrophobins seems to depend on a conformational change in the molecules during assembly into an amphipathic film rather than on a diffusion-limited adsorption to the interface (van der Wegt et al., 1996, Wösten and Wessels, 1997). Similarly to SC3 hydrophobin also HFBI and HFBII hydrophobins of *T. reesei* have been shown to reduce water surface tension (our unpublished results). The decreased surface tension leads to more stable gas bubbles, thus hydrophobins and other amphibatic polypeptides stabilise foam.

Hydrophobin-like molecules vary in their properties. For example, rodlet-forming capacity has not been attributed to all hydrophobins (such as some class II), or they might have a weaker tendency to form stable aggregates (Russo et al., 1982; Carpenter et al., 1992). Another group of fungal amphiphatic proteins are repellents (Kershaw and Talbot, 1998). Other type of proteins and polypeptides responsible for foam formation may consequently have only some of the features attributed to hydrophobins. Such examples are SapB and streptofactin, which are surface-active peptides secreted into the culture medium by *Streptomyces coelicor* and *S. tendae*, respectively (Willey et al., 1991, Richter et al., 1998).

Very little is known about the 2D and 3D structures of hydrophobins and the changes that occur upon self-assembly. However both hydrophobin classes are speculated to contain two domains which are stabilised by two disulfide bridges (Wösten and Wessels, 1997).

Strategies to find and inactivate hydrophobins and other hydrophobic/amphipathic proteins and polypeptides are well known in the art and include techniques such as screening of genomic or cDNA libraries with hybridization techniques using homologous/heterologous DNA fragments and oligonucleotides designed on the basis of conserved regions in the protein/peptide encoding region. The sequence diversity of hydrophobins means, however, that isolation of hydrophobin-like genes on the basis of sequence homology may prove difficult. Few reports exist in which nucleic acid similarity has been exploited to isolate a hydrophobin gene using heterologous hybridization (e.g. Muñoz et al. 1997).

However, several techniques exploiting purified protein for isolation of the corresponding gene are known to a person skilled in the art. After proteins, polypeptides or peptides associated with foam formation have been purified, the corresponding genes are isolated using suitable techniques such as e.g. screening of expression libraries using antibodies raised against purified proteins, or PCR cloning or screening of genomic and/or cDNA libraries using oligonucleotides designed on the basis of N-terminal or internal protein sequences.

Proteins, polypeptides, or peptides associated with foam formation may be purified on the basis of their properties. They can be recovered from the foam formed during the cultivation of a strain or caused by bubbling gas through the medium. Foam-associated proteins, polypeptides and peptides may further be recovered from aggregates caused by freezing of culture medium. Proteins, polypeptides or peptides, the prevention of whose production is useful according to the present invention, can also be obtained by applying the cells, cell extracts or culture media of a strain to aqueous two-phase system (ATPS) and recovering the proteins separated into the phase containing the hydrophobic phase material as shown for hydrophobins (Hyytiä et al. 1999).

According to this invention a microorganism strain is genetically modified not to produce an essential amount of at least one of the proteins or polypeptides or peptides associated with foam formation during the cultivation of the non-modified microorganism host. An essential amount means here that the host strain produces at least 50% less amphipathic proteins, polypeptides or peptides, preferably 60-80%, most preferably 80-100% less amphipathic proteins, polypeptides or peptides compared to the non-modified parent host strain.

Decreasing the level of foam formation during cultivation means here that the foam formation is lowered at least 30%, preferably 40-80%, most preferably 80-100% compared to the foam formation during cultivation of the non-modified parent host strain.

The decreased foam formation results in savings of antifoam agents and increase in fermentation working volume. The saving of antifoam agent is at least 30%, preferably 40-80%, most preferably 80-100%. The increase in fermentation working volume is at least 5%, preferably 10-20%.

An increased capability to produce a product of interest means here that a production host modified not to produce an essential amount of at least one of amphipathic or hydrophobic proteins, polypeptides or peptides, is capable of producing at least 1.2 times, preferably at least 2, more preferably at least 3, still more preferably at least 5, most preferably 10 times higher amount of a product than a host not modified according to this invention. The product may be recovered from the cultivation, from the cells or from the culture medium, preferably it is recovered from the culture medium.

A deletion vector denotes here a vector comprising a DNA sequence encoding a marker gene and so called flanking regions, which make it possible to delete the desired gene from the production host genome and replace it by the marker gene. The marker gene may be amd S from *Aspergillus nidulans*, hph from *E. coli*, or any other dominant or auxotrophic selection marker known in the literature. The vector may be a cloning vector from the pUC series or any other generally available cloning vector. The deletion cassette (comprising the DNA sequence encoding the chosen marker gene and flanking regions) is removable from the vector genome by restriction enzymes.

The present invention was exemplified by inactivating one or more DNA sequences encoding hydrophobins in fungal host strains. The inactivation of already one of the DNA sequences encoding hydrophobins significantly affected foam formation.

In particular, the present invention was exemplified by the deletion of hfb1 and/or hfb2 genes from the *Trichoderma reesei* genome. The cloning and isolation of these genes and purification of the corresponding proteins HFBI and HFBII has been described in the PhD Thesis of Nakari-Setälä (Nakari-Setälä, T., VTT Publications 254, Espoo 1995) (Nakari-Setälä et al. 1996; Nakari-Setälä et al. 1997) In the Thesis HFBI and HFBII of *T. reesei* were speculated to play a role in attachment to substrates or to contribute to spore hydrophobicity, but the biological roles of these proteins was largely unknown before this invention. Hence their significant role in foam formation during fermentation as shown in the present invention was a surprising feature. In the present invention it was shown that the deletion of already one of the genes encoding hydrofobins in the genome of *Trichoderma reesei* resulted in remarkable decrease of foam formation during fermentation of a modified *Trichoderma* host.

In order to delete hfb1 and hfb2 genes from *Trichoderma reesei* genome, vectors comprising a deletion of these genes were constructed. In the vector hfb1 gene was replaced by amdS gene and in the vector hfb2 gene was replaced by hph gene of *E. coli* coding for hygromycin B. The cloning vector was one of the vectors of the pUC series, pUC 18.

Different *T. reesei* strains (QM 9414 and Rut-C-30) were transformed with the deletion vectors by transformation methods known in the art as described in Example 2 and the removal of the hfb genes in the transformants obtained was confirmed. The transformants having deletion of hfb1, hfb2, or both were cultivated in shake flasks on different growth media with glucose, sorbitol and lactose as carbon sources. The results showed that the deletion of hfb1, hfb2 or both genes had no negative effect on the production of enzymes by *T. reesei*. In some cases the enzyme production was even better than with the parental *T. reesei* strain.

As a result of the hfb1 gene deletion, the cell walls, the Δhfb1 hyphae grown on glucose in shake flasks cultivations look thinner than the control hyphae, and the strain also formed large pellets during cultivation. The growth of the transformant was somewhat impaired in the middle of the cultivation but the deletion strain reached the host strain at later stages of the cultivation. Deletion of the hfb2 gene did not have effect on the morphology of the transformant when grown on lactose in shaken liquid cultures and no difference in growth was detected inbetween the transformant and the host strain.

*T. reesei* Rut C30 strain modified to have deletion of hfb2 in its genome was also grown on lactose and cellulose in a fermentor. The consumption of the antifoam agent, pH, growth and protein and enzyme production was monitored. The results clearly showed that deletion of a single hydrophobin gene significantly decreased the foam formation. Especially in the cultivation of *T. reesei* Rut-C30 on cellulose, in which the cultivation medium contains insoluble cellulose polymers, large amount of rather stable foam was formed and therefore antifoam consumption was high. The cultivation of the transformant on lactose did not utilise any antifoam agent and on cellulose the amount of antifoam needed during the cultivation was only 12% of that of the control cultivation. The decreased consumption of antifoam has several positive effects. The major advantage is a much easier downstream processing.

The deletion of the hfb2 gene had no significant effect on growth of the transformant strain in fermentor in the tested conditions. Nor had the deletion of the hfb2 gene any clear negative effect on extracellular protein and enzyme production by the transformant.

In contrast in a transformant strain having at least one deletion the production of total secreted protein was enhanced. The production of protein per biomass as measured by protein and protease amount was significantly greater when compared to a non-deletion strain.

The production of a protein product was here also exemplified by producing fusion molecules comprising a hydrophobin-like protein. A production host strain was modified not to produce proteins or polypeptides associated with foam formation and the same host was transformed to produce a fusion molecule comprising an amphipathic protein and a molecule of interest for further purification in aqueous two-phase system (ATPS). The following examples are for illustration of the present invention and should not be construed as limiting the present invention in any manner.

EXAMPLES

Example 1

Construction of Vectors for Deletion of hfb1 and/or hfb2 Genes from the *Trichoderma reesei* Genome For deletion of hfb1 (SEQ ID 1, FIG. 1) gene from *T. reesei* genome, a plasmid was constructed in which the hfb1 coding region was replaced by the amdS gene of *Aspergillus nidulans* coding for acetamidase. Plasmid pEA10 (Nakari-Setälä et al. Eur. J. Biochem. (1996) 235:248-255) carrying ca. 5.8 kb SalI fragment containing the hfb1 coding and flanking regions was digested with MunI and blunted with T4 DNA polymerase. The subsequent vector fragment missing the ca. 950 bp MunI fragment containing the coding and some flanking regions for hfb1 was purified from agarose gel and ligated to a 3.2 kb amdS fragment released from p3SR2 (Hynes et al. Mol. Cell Biol. (1983) 3:1430-1439; Tilburn et al. Gene (1983) 26:205-221) with SphI and XbaI and blunted with T4 DNA polymerase. The resulting plasmid is pTNS24 (FIG. 3). It carries a deletion casette containing the amdS gene with ca. 2.7 kb and 2 kb of the hfb1 5' and 3' non-coding regions, respectively. The deletion casette may be released from the vector with SalI.

Figure 4:
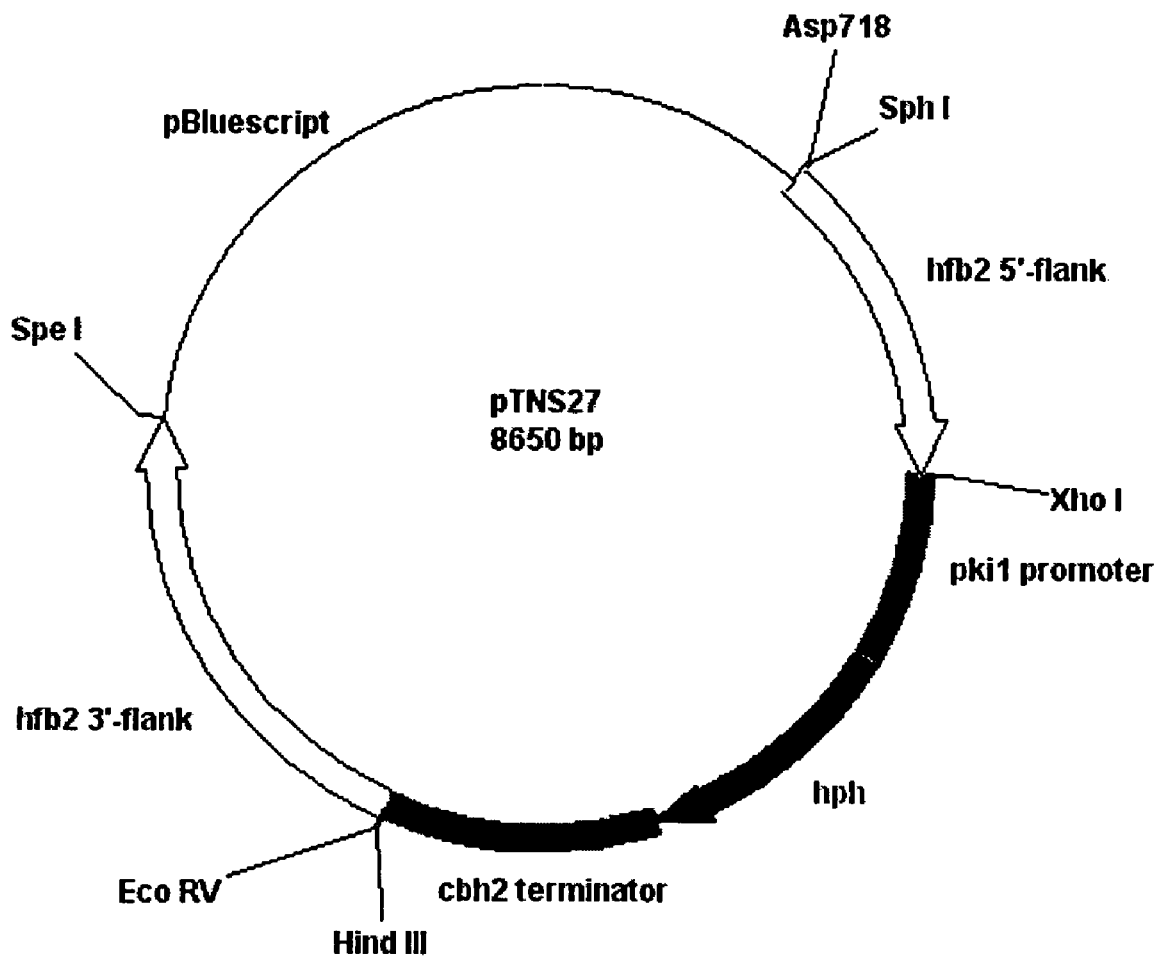
FIG. 4 depicts plasmid pTNS 27

For removal of the hfb2 (SEQ ID 2, FIG. 2) gene from *T. reesei* genome, a plasmid was constructed in which the hfb2 coding region was replaced by the hph gene of *E. coli* coding for hygromycin B phosphotransferase. A 1.2 kb 5' flanking region of the hfb2 gene was released from the plasmid pTNS8 (Nakari-Setälä et al. Eur. J. Biochem. (1997) 248: 415-423) with HindIII and BglI, blunted with T4 DNA polymerase and purified from agarose gel. The purified fragment was ligated to pARO21 (Penttilä et al. Patent appl. FI 990667) cut with XhoI and blunted with T4 DNA polymerase resulting in pTNS26. pARO21 is essentially the same as pRLMex30 (Mach et al. Curr. Genet. (1994) 6:567-570) and carries the *E. coli* hph gene operably linked to 730 bp of pki1 promoter and 1 kb of cbh2 terminator sequences of *T. reesei*. To introduce the 3' flanking region of hfb2 into the deletion casette, pTNS26 was cut with EcoRV, treated with SAP (shrimp alkaline phosphatase, Boehringer-Mannheim) and ligated to a 1.7 kb EcoRV hfb2 3' flanking region fragment released from pTNS8. In the resulting plasmid pTNS27 (FIG. 4) both the 5' and 3' non-coding regions of the hfb2 gene flank the hph expression casette in the same orientation. The deletion casette may be released from the vector with SphI and SpeI.

Example 2

Transformation of *Trichoderma* and Purification of Δhfb Clones

*Trichoderma reesei* strains QM9414 (VTT-D-74075), Rut-C30 (VTT-D-86271) and QM9414 Δhfb1 (VTT-D-99724) were transformed essentially as described (Penttilä et al., Gene (1987) 61:155-164) using 3-13 μg of the plasmids pTNS24 and pTNS27 or the deletion casettes released from them with the proper restriction enzymes.

The Amd+ and Hyg+ transformants obtained were streaked three times onto plates containing acetamide and hygromycin, respectively (Penttilä et al. (1987) Gene 61:155-164). Thereafter spore suspensions were made from transformants grown on Potato Dextrose agar (Difco).

To confirm the removal of the hfb genes from the genomes, Southern analyses were carried out. Mixed Amd+ and Hyg+ transformants were cultivated on minimal medium (Penttilä et al. (1987) Gene 61:155-164) containing 3% glucose and 0.2% peptone for isolation of genomic DNA using Easy-DNA kit (Invitrogen). Approximately 2 μg of DNA were cleaved with PvuI in the case of Δhfb1 transformants and with NcoI in the case of Δhfb2 transformants. Southern hybridizations with ca. 5.8 kb and 3.8 kb genomic fragments containing hfb1 and hfb2 genes and flanking regions were carried out. In the host strain, the hybridization with the probes results in both cases in one large signal whereas in transformants two smaller signals are obtained if the hfb gene has been correctly deleted.

The spore suspensions of the clones from which the hfb genes had been deleted on the basis of Southern analysis were purified to single spore cultures on selection plates (containing either acetamide or hygromycin). Southern analysis was repeated similarly as above to select pure Δhfb clones.

*T. reesei* strains used for further studies are VTT-D-99724 and VTT-D-99723 (QM9414 Δhfb1), VTT-D-99726 (QM9414 Δhfb2), VTT-D-99725 (QM9414 Δhfb1Δhfb2) and VTT-D-99676 (Rut-C30 Δhfb2).

Example 3

Enzyme Production of *Trichoderma* QM9414 of Δhfb1, Δhfb2 and Δhfb1Δhfb2 Strains on Glucose, Sorbitol and Lactose Strains VTT-D-99724 (Δhfb1), VTT-D-99726 (Δhfb2), VTT-D-99725 (Δhfb1Δhfb2) and their host strain VTT-D-74075 (QM9414) were cultivated in shake flasks at 28° C. for three and seven days in 50 ml of *Trichoderma* minimal medium (Penttilä et al. 1987) supplemented with 0.2% peptone and as a 2% carbon source either i) glucose, ii) sorbitol or iii) lactose. Starting pH was pH 4.8. Culture medium samples were taken after 3 of cultivation. Secreted total proteins were analysed by the method of Lowry et al. 1951. Endoglucanase and endoxylanase activities were measured according to IUPAC standard method and Bailey et al. (1992) using hydroxyethyl celluose (HEC, Fluka 54290) and birch xylan (XYL, Roth 7500) as substrates, receptively. Protease activity was determined semi-quantitatively by dotting 5 μl of culture filtrates on 1.5% agar plates (pH 5) containing 1% skim milk and estimating the size of the halos due to protease activity in the samples.

The values obtained from activity measurements and calculated as enzyme activity per total secreted protein are presented in the table below. These figures indicate that deletion of hfb genes has no negative, but in some cases even positive, effect on production of both glycanases and proteanases, two groups of enzymes whose expression is under different regulatory mechanisms. Culture broth pH values at the end of the cultivation indicate that on the same culture medium all strains are approximately in the same growth stage. No clear differences were seen visually in morphology or amount of cell mass inbetween the different strains on same medium.

| Strain | Carbon source | HEC nkat/mg total protein | XYL nkat/mg total protein | Protease |
|---|---|---|---|---|
| Host QM9414 | Glucose | nd | nd | + |
| Δhfb1 | | nd | nd | +++ |
| Δhfb2 | | nd | nd | + |
| Δhfb1Δhfb2 | | nd | nd | ++ |
| Host QM9414 | Sorbitol | – | 30 | – |
| Δhfb1 | | – | 50 | – |
| Δhfb2 | | – | 60 | – |
| Δhfb1Δhfb2 | | – | 63 | – |
| Host QM9414 | Lactose | 78 | 253 | – |
| Δhfb1 | | 98 | 202 | – |
| Δhfb2 | | 89 | 363 | – |
| Δhfb1Δhfb2 | | 92 | 190 | – | nd, not determined
–, not detected

Example 4

Growth and Morphology of *T. reesei* QM9414 Δhfb1 Strain on Glucose

The strains VTT-D-99724 (Δhfb1) and VTT-D-99723 (Δhfb1) originating from two independent transformants and their host strain VTT-D-74075 (QM9414) were also cultivated in shake flasks at 28° C. for five days in 250 ml of *Trichoderma* minimal medium (Penttilä et al. 1987) buffered to pH 6 and supplemented with 3% glucose. The growth of the strains was followed by measuring the mycelial dry weights and qualitatively from the pH values of culture media at different time points.

Figure 10:
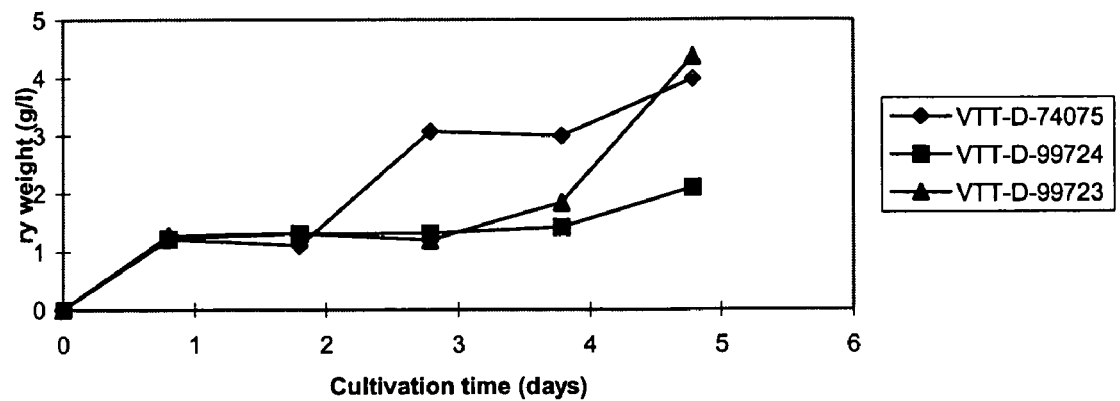
FIG. 10 depicts biomass production of the strains VTT-D-74075, VTT-D-99724 and VTT-D-99723 in shake flask cultivation on glucose medium.
Figure 11:
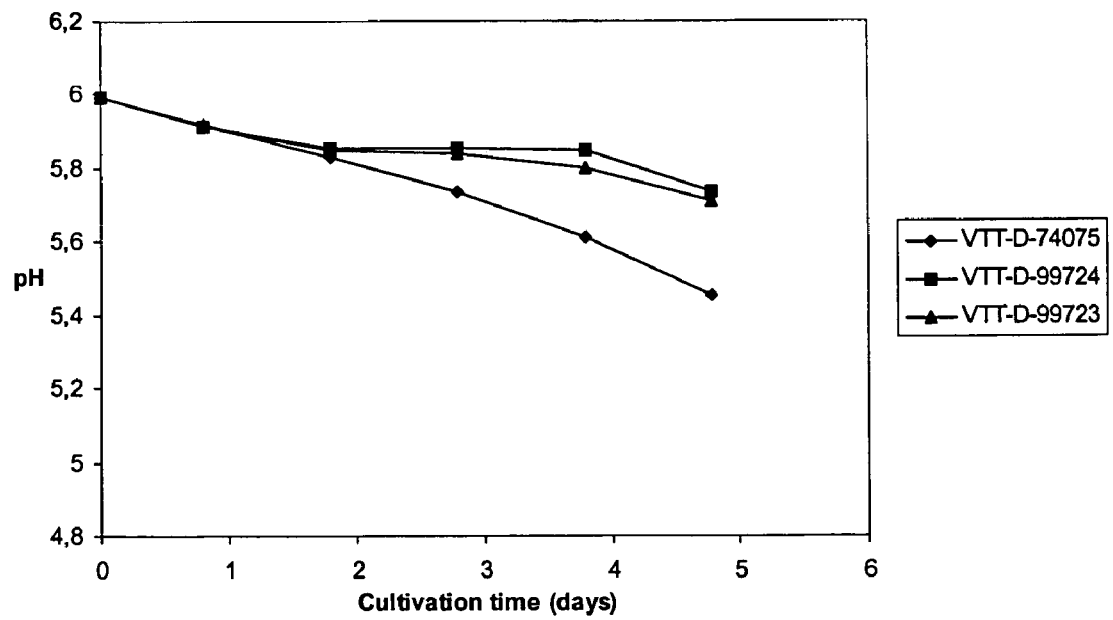
FIG. 11 depicts growth of the strains VTT-D-74075, VTT-D-99724 and VTT-D-99723 in shake flask cultivation on glucose medium represented as a change in pH during the cultivation.

As a result of the hfb1 gene deletion, the ability of *T. reesei* to grow on glucose was impaired in shaken liquid cultures as can be seen from the mycelial dry weight (FIG. 10) and pH (FIG. 11). The appearance of the hyphae in the glucose cultivation was monitored with a light microscope to study the morphology of the deletion strains. Probably due to the lack of HFBI protein in the cell walls, the Δhfb1 hyphae looked thinner than the control hyphae, and the strain also formed large pellets during cultivation. However, it should be noted that during the time course of the cultivation the deletion strain VTT-D-99723 reaches the host strain in terms of biomass production.

Example 5

Cultivation of *Trichoderma* Rut C30 Δhfb2 Strain on Lactose in Shake Flasks

Figure 12:
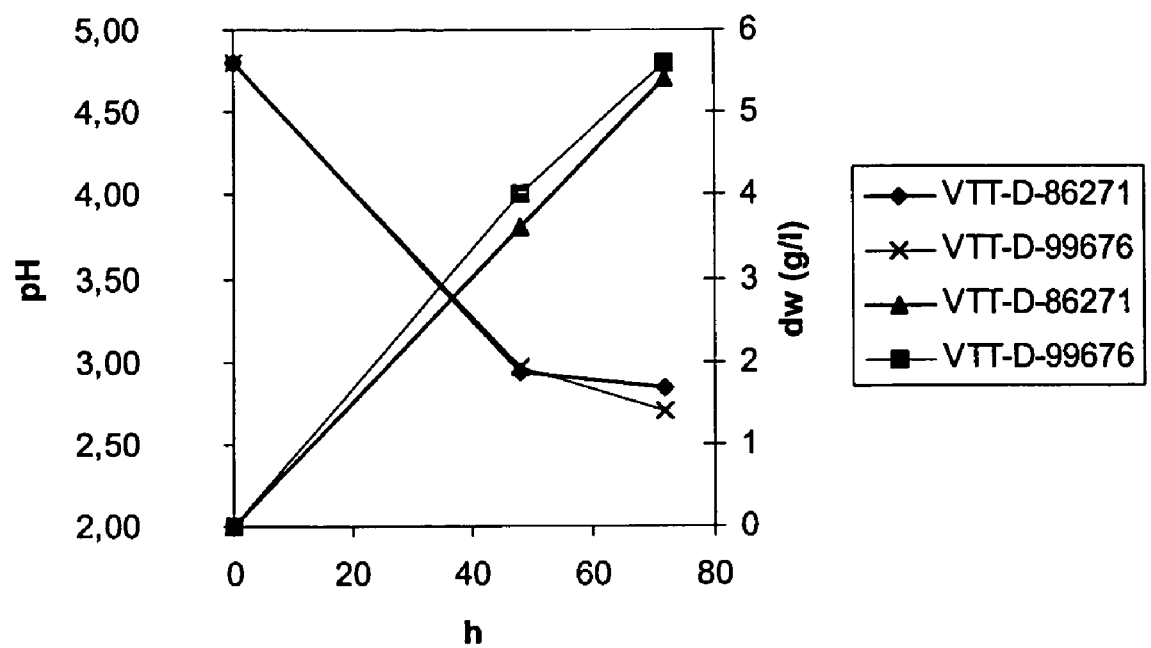
FIG. 12 depicts growth of the strains VTT-D-86271 and VTT-D-99676 in shake flask cultivation on lactose medium represented by biomass production and pH.

Strain VTT-D-99676 (Δhfb2) and its host strain VTT-D-86271 (Rut-C30) were cultivated at 28° C. in shake flasks for three days in 250 ml of *Trichoderma* minimal medium (Penttilä et al. 1987) buffered to pH 6 and supplemented with 0.2% peptone and 2% lactose with lactose feeding. Samples were taken from the flasks on days 2 and 3 for analysis of growth and protein production. Growth was analysed quantitatively by measuring the mycelial dry weight and qualitatively from pH values of culture medium. No differences in growth were detected inbetween the transformant and the host strain on the basis of these measurements as seen in FIG. 12. Also, the morphology of the transformant strain was similar to that of the host strain.

Production levels of secreted endoglucanases (HEC) and cellobiohydrolases (MUL) measured according to IUPAC standard method and Tilbeurgh et al. (1988), respectively, are presented in the table below. The results clearly show that the deletion of the hfb2 gene from the control strain had no negative effect on enzyme production.

| Strain | h | dry weight g/l | HEC nkat/ml | MUL nkat/ml |
|---|---|---|---|---|
| VTT-D-86271 | 0 | 0 | 0 | 0 |
| | 48 | 3.6 | 230 | 3.2 |
| | 72 | 5.4 | 247 | 9 |
| VTT-D-99676 | 0 | 0 | 0 | 0 |
| | 48 | 4 | 236 | 2.7 |
| | 72 | 5.6 | 214 | 7 |

Example 6

Cultivation of *Trichoderma* Rut C30 Δhfb2 Strain on Lactose in Fermenter

Modern cellulose production media may for some, but not all strains be based on lactose as the carbon source and enzyme inducer. The control strain Rut-C30 produces cellulases efficiently on lactose, whereas e.g. the strain QM9414 does not.

*Trichoderma reesei* Rut-C30 and its Δhfb2 transformant VTT D-99676 (D-676) were cultivated on lactose-based medium in a 15 liter laboratory fermenter. The medium contained (in g l$^{-1}$) lactose (Riedel-de Haën, Germany, product 33411) 40, peptone (Difco, USA, 0118-17) 4.0, yeast extract (Difco, 0127-17), 1.0, $KH_2PO_4$ 4.0, $(NH_4)_2SO_4$ 2.8, $MgSO_4 \times 7H_2O$ 0.6, $CaCl_2 \times 2H_2O$ 0.8 (sterilised separately) and 2.0 ml l$^{-1}$ of a trace solution (Mandels and Weber 1969). No antifoam agent was added to the medium before the in-situ sterilisation (123° C./20 min). Cultivation conditions were: temperature 29° C., agitation 600 rpm, aeration 10 l min$^{-1}$, pH 4.0 . . . 5.0.

In these cultivations on the completely soluble medium, it was possible to monitor growth by analysis of biomass dry weight and by consumption of lactose. A comparison of the growth parameters in the two cultivations is presented in FIGS. [8] A and B. The results clearly showed that deletion of the hfb2 gene from the control strain had no significant effect on growth. Foaming was not a major problem on this medium with either strain. Consumption of antifoam agent was 10 ml/15 liters with strain Rut-C30, whereas no antifoam agent at all was consumed in the cultivation of strain D-676.

In this pair of cultivations, cellulase production by the Δhfb2 strain was somewhat lower than by the control strain Rut-C30 (Table below). However, experience with cellulase production on lactose-based media has shown that optimisation of process conditions must be performed for each producing strain separately. The effects of incipient catabolite repression due to cleavage of the lactose molecule to glucose and galactose must be avoided by suitable, strain-specific adjustment of pH and/or temperature.

Table. Production of soluble protein, cellulases (HEC, FPU, IUPAC standard method) and overall consumption of antifoam agent (Struktol J633) in cultivations of *T. reesei* Rut C30 and its Δhfb2 transformant VTT D-99676 on lactose medium in a 15 liter laboratory fermenter.

| Strain | Dry weight g l$^{-1}$ | Protein g l$^{-1}$ | HEC nkat ml | FPU u ml$^{-1}$ | Antifoam consumption ml l$^{-1}$ |
|---|---|---|---|---|---|
| Rut-C30 | 15.8 | 5.9 | 780 | 3.5 | 0.7 |
| VTT D-99676 | 14.6 | 5.0 | 610 | 2.1 | 0.0 |

Example 7

Cultivation of *Trichoderma* Rut C30 Δhfb2 Strain on Cellulose in Fermenter

*Trichoderma reesei* Rut C30 and its Δhfb2 transformant VTT D-99676 (D-676) were cultivated on cellulose-spent grain medium in a 15 liter laboratory fermenter. The medium contained (in g l$^{-1}$) Solka floc cellulose 40, distiller's spent grain 20, KH$_2$PO$_4$ 5 and (NH$_4$)$_2$SO$_4$ 5. A standard dose of 5 ml antifoam agent (Struktol J633, Schill&Seilacher, Hamburg, Germany) was added to the medium to prevent foaming during the in-situ sterilisation (123° C./20 min). Cultivation conditions were: temperature 29° C., agitation 600 rpm, aeration 10 l min$^{-1}$, pH 4.0 . . . 5.0.

Growth in terms of biomass production or substrate consumption could not be measured on the solids-based medium, but production curves of cellulase (HEC; FPU) and soluble protein (Lowry et al. 1951) indicated rather similar rates and levels of production by the control and transformant strains (FIGS. [9] A and B). The curves of broth pH are also presented in the figure as an indication of the sequence of growth phases: first indeterminate or increasing trend during the lag phase and early growth, decreasing pH during the main growth phase and finally an increasing trend during secondary metabolism/starvation. Production levels of the cellulase and xylanase activities measured in the cultivations are presented in Table below. These results clearly show that deletion of the hfb2 gene from the control strain had no negative effect on enzyme production. Due to the unhomogenous nature of all the enzyme substrates used in this comparison, typical variation in analysis results is in the region of ±10% for HEC and XYL and at least 15-20% for FPU.

Table. Production of soluble protein, cellulases (HEC, FPU, IUPAC standard method) and xylanase (XYL, Bailey et al. 1992) and overall consumption of antifoam agent (Struktol J633) in cultivations of *T. reesei* Rut C30 and its Δhfb2 transformant VTT D-99676 on cellulose-spent grain medium in a 15 liter laboratory fermenter.

| Strain | Protein g l$^{-1}$ | HEC nkat ml | FPU u ml$^{-1}$ | XYL nkat ml$^{-1}$ | Antifoam consumption ml l$^{-1}$ |
|---|---|---|---|---|---|
| Rut C30 | 13.9 | 1600 | 10.9 | 1870 | 3.3 |
| VTT D-99676 | 16.4 | 1715 | 8.9 | 2240 | 0.4 |

The major, striking difference between the two cultivations was in the consumption of antifoam agent: in the control cultivation with strain Rut C30 consumption of Struktol was 50 ml/15 liters, whereas in the case of strain D-676 only 6.0 ml was consumed. Apparently the latter cultivation foamed only on one occasion, towards the very end of the run. This foaming was presumably the result of the secretion of enzyme proteins into the medium, which was obviously independent of the presence or absence HFBII. The almost tenfold difference in the requirement for antifoam agent would certainly have a significant effect on industrial scale downstream processing (enzyme concentration by membrane filtration and possible chromatographic purification).

Example 8

Cultivation of Δhfb1Δhfb2 *Trichoderma* QM9414 Strain on Glucose in Fermenter

*Trichoderma reesei* strain QM9414 (VTT-D-74075) and its Δhfb1Δhfb2 transformant VTT D-99725 were cultivated on glucose-based medium in a 15 liter laboratory fermenter. The medium contained (in g l$^{-1}$) glucose, 40, peptone (Difco, USA, 0118-17) 4.0, yeast extract (Difco, 0127-17), 1.0, KH$_2$PO$_4$ 4.0, (NH$_4$)$_2$SO$_4$ 2.8, MgSO$_4$x7H$_2$O 0.6, CaCl$_2$x2H$_2$O 0.8 (sterilised separately) and 2.0 ml l$^{-1}$ of a trace solution (Mandels and Weber 1969). No antifoam agent was added to the medium before the in-situ sterilisation (123° C./20 min). Cultivation conditions were: temperature 29° C., agitation 600 rpm, aeration 10 l min$^{-1}$, pH 4.0 . . . 5.0. Morphology, biomass dry weight, pH, oxygen and antifoam agent consumption and production of extracellular protein (Lowry et al. 1951) and protease activity using the method based on hydrolysis of Azurine casein (Protazyme AK kit, Megazyme) was analysed during the cultivations.

Figure 13A:
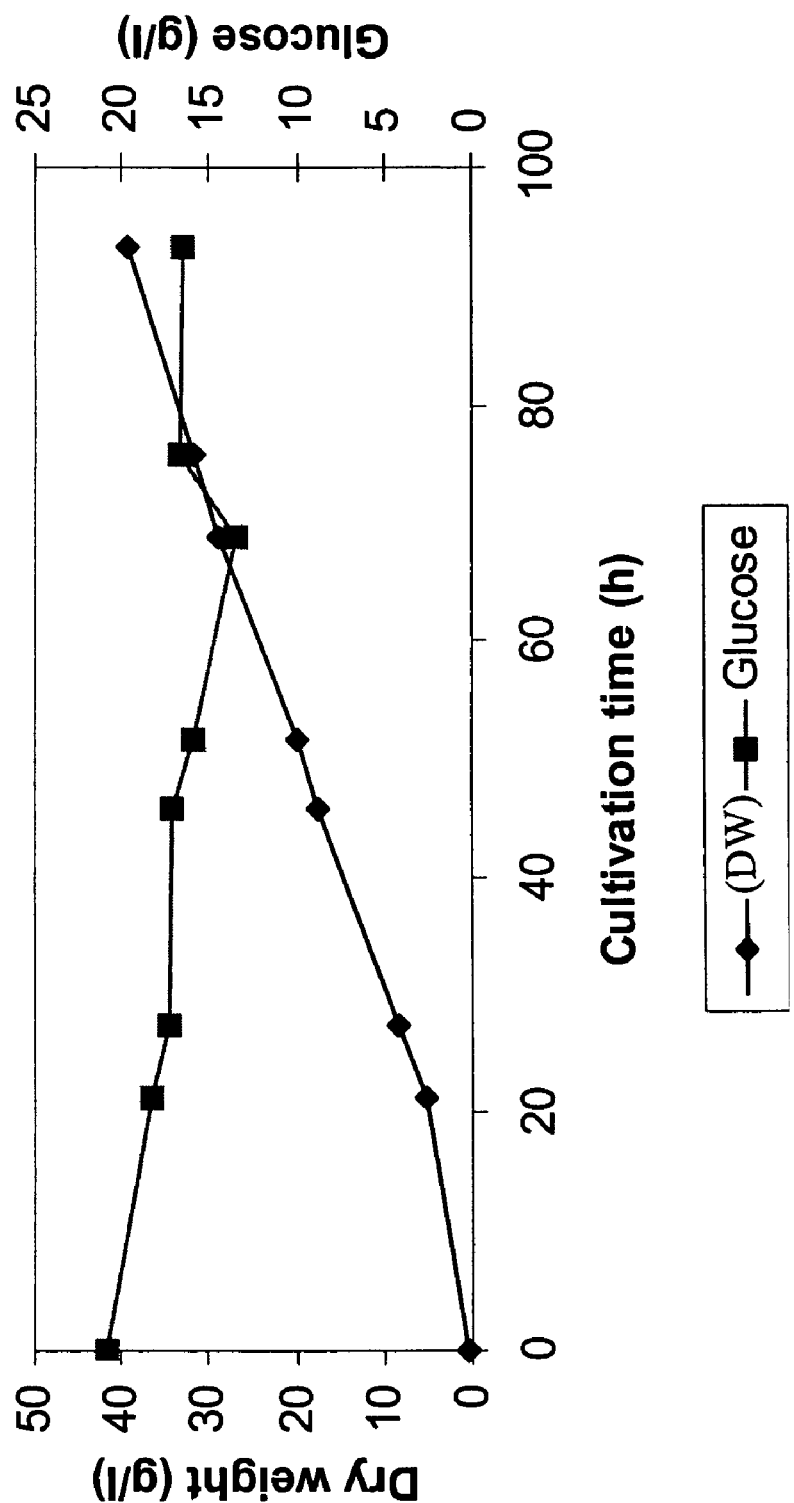
FIGS. 13A and 13B depicts growth parameters of *Trichoderma* strains in a fermentor cultivation on glucose.
Figure 13B:
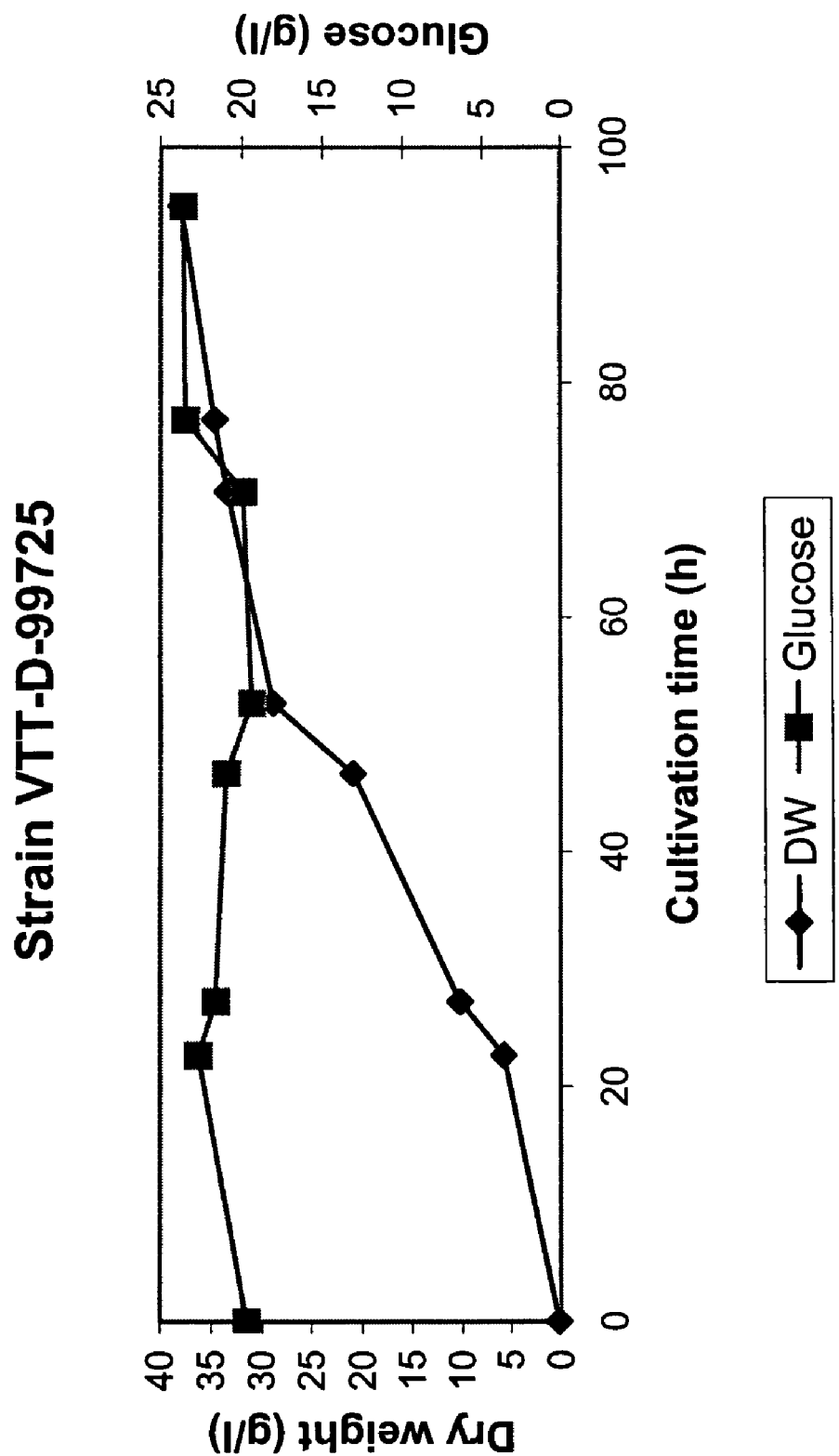

Growth in terms of biomass production and substrate consumption indicated rather similar growth of the control and transformant strain (FIGS. 13 A and B). No remarkable differences in morphology were detected between the strains. Production of total soluble protein and level of protease activity as an example of more specific secreted activity are presented in Table below. The major difference between the two strains was in the production of total secreted protein. In the cultivation with the unmodified strain QM9414 0.062 g/l of protein was measured while the modified strain VTT-D-99725 produced 0.390 g/l soluble proteins. Thus production of protein per biomass as measured by protein and protease amount was significantly greater.

Table. Production of biomass, soluble protein and proteases at the end of the cultivations of *T. reesei* QM9414 and its Δhfb1Δhfb2 transformant VTT D-99725 on glucose medium in a 15 liter laboratory fermenter.

| Strain | Biomass gl$^{-1}$ | Protein gl$^{-1}$ | Protease A$_{590\,nm}$ |
|---|---|---|---|
| QM9414 | 39.3 | 0.062 | 0.205 |
| VTT-D-99725 | 38.0 | 0.390 | 0.268 |

Example 9

Production of EGIcore-HFBI Fusion Proteins in *T. reesei* Δhfb2 Strain for Improved Partitioning of the Fusion Protein in ATPS For construction of an EGIcore-HFBI fusion protein, the hfb1 coding region from Ser-23 to the STOP codon was amplified with PCR with the following primers, as a 5' primer ACT ACA CGG AG <u>GAGCTC</u> G ACG ACT TCG AGC AGC CCG AGC TGC ACG CAG AGC AAC GGC AAC GGC (SEQ ID No 3) and as a 3' primer TCG TAC GGATCC TCA AGC ACC GAC GGC GGT. (SEQ ID No 4) The sequence in bold in the 5' primer encodes amino acids 410-425 in EGI and the underlined GAGCTC is a SacI site. The 260 bp PCR fragment was purified from agarose gel and ligated to pPCRII T/A vector (Invitrogen) resulting in pMQ111.

Figure 5:
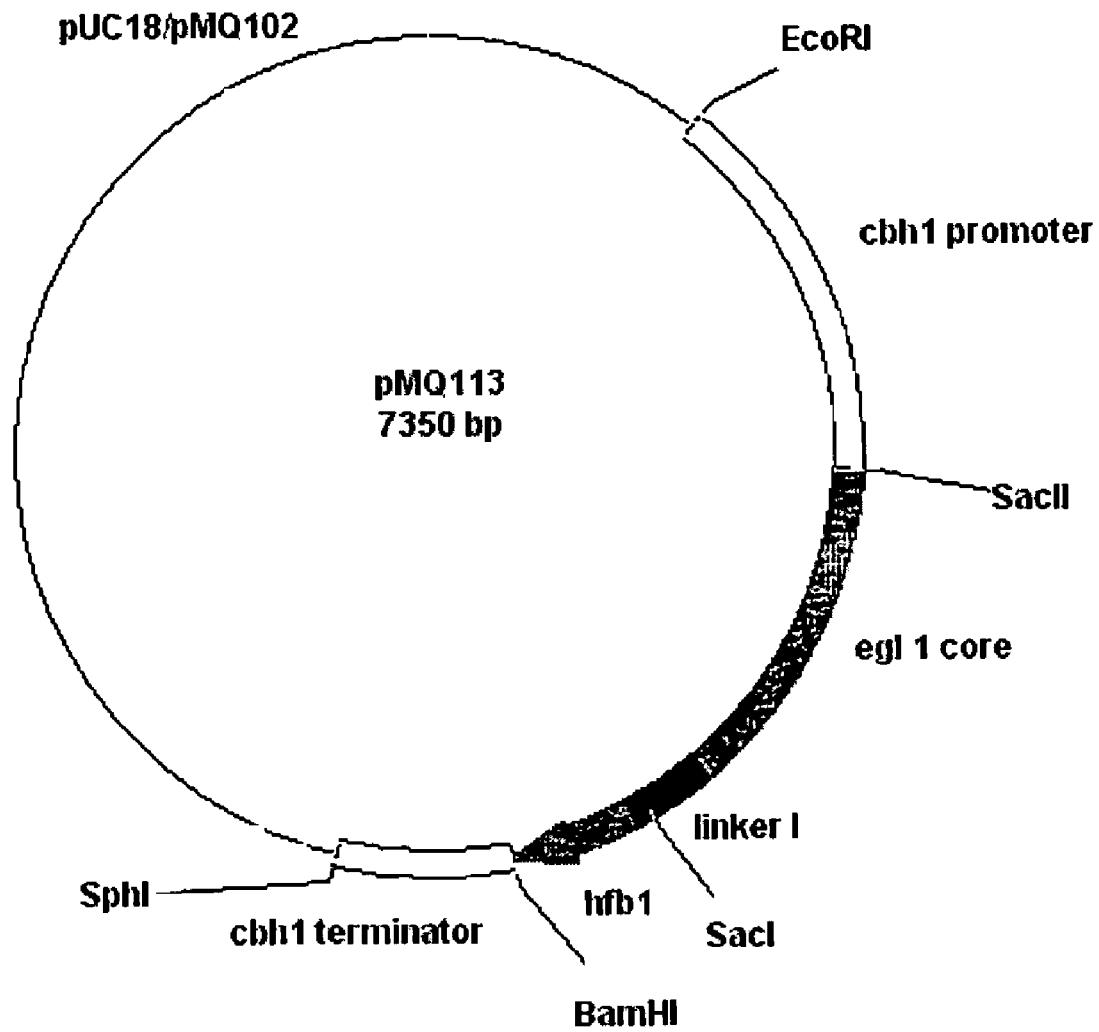
FIG. 5 depicts plasmid pMQ113

In the next step *Trichoderma* expression vectors for production of EGIcore-HFBI fusion protein under the control of cbh1 promoter and terminator sequences was constructed. The expression vector used as a backbone in the constructs is pPLE3 (Nakari et al. (1994) WO 94/04673) which contains a pUC18 backbone, and carries the cbh1 promoter inserted at the EcoRI site. The cbh1 promoter is operably linked to the full length egl1 cDNA coding sequence and to the cbh1 transcriptional terminator. The plasmid pMQ111 was digested with SacI and BamHI and the 260 bp fragment containing the hfb1 sequence was ligated to pPLE3 digested with SacI and BamHI. The resulting plasmid pMQ113 (FIG. 5) carry the coding sequences for EGIcore linked to HFBI via its own linker region under the control of cbh1 promoter and terminator sequences.

*Trichoderma reesei* strain QM9414 Δhfb2 (VTT-D-99726) was transformed essentially as described (Penttilä et al., Gene (1987) 61:155-164) using 10 μg of the plasmid pMQ113 together with 3 μg of the selection plasmid pTOC202 containing the amdS gene (Hynes et al. Mol. Cell. Biol. (1983) 3:1430-1439; Tilburn et al. Gene (1983) 26:205-221) of *Aspergillus nidulans* encoding for acetamidase.

The Amd+ transformants obtained were streaked two times onto plates containing acetamide (Penttilä et al. (1987) Gene 61:155-164). Thereafter spore suspensions are made from transformants grown on Potato Dextrose agar (Difco). The production of the EGIcore-HFBI fusion protein is tested by slot blotting or Western analysis with EGI and HFBI specific antibodies from shake flask or microtiter plate cultivations carried out in minimal medium supplemented with a mixture of Solka floc cellulose and/or spent grain and/or whey. The spore suspensions of the clones producing fusion protein are purified to single spore cultures on selection plates (containing acetamide). To determine the best producers, production of the fusion protein is analyzed again from these purified clones as described above.

For partitioning experiments of the EGIcore-HFBI fusion protein in ATPS using the polyoxyethylene detergent $C_{12-18}$ $EO_5$ (Agrimul NRE 1205, Henkel) the best production strain obtained in this study and as control strains VTT-D-98691 (QM9414 strain producing EGIcore-HFBI), VTT-D-74075 (QM9414) and VTT-D-99726 (QM9414 Δhfb2) are cultivated at 28° C. in shake flasks for 5 to 6 days in 50 to 250 ml volume of *Trichoderma* minimal medium (Penttilä et al. 1987) supplemented with 3% Solka floc cellulose and 1% spent grain.

Partitioning experiments are carried out with supernatant (biomass separated by centrifugation or filtration) in 10 ml graduated tubes. First detergent is added into the tubes and the tubes are then filled to 10 ml with culture supernatant. The amount of detergent in the tube is calculated in weight percent of detergents. After thorough mixing in an overhead shaker the separation takes place by either gravity settling in a water bath at constant temperature or by centrifugation at constant temperature. The separation is usually performed at 30° C., the standard amount of detergent used is 2-5% (w/v). After separation the volume ratio of the lighter and heavier phase is noted and the concentration factor for the fusion protein is calculated from it. Samples are also taken from the lighter and heavier phase for analysis.

Two-phase separations are analysed qualitatively by using SDS-PAGE gels followed by visualization of the fusion proteins with Coomassie brilliant blue R-250 (Sigma) or Western blotting. Polyclonal anti-HFBI antibody are used in Western analysis for detection of EGIcore-HFBI protein together with alkaline phosphatase conjugated anti-rabbit IgG (Bio-Rad). Alkaline phosphatase activity is detected calorimetrically with BCIP (5-bromo-4-chloro-3-indolyl-phosphate) used in conjunction with NBT (nitro blue tetrazolium) (Promega).

EGI activity is detected using 4-methylumbelliferyl-β-D-cellobioside (MUC) (Sigma M 6018) as substrate (Van Tilbeurgh H. & Caeyssens M., 1985; Van Tilbeurgh et. al., 1982). EGI hydrolyses the β-glycosidic bond and fluorogenic 4-methylumbelliferone is released, which can be measured using a fluorometer equipped with a 360 excitation filter and a 455 nm emission filter. CBHI also hydrolyses the substrate and it is inhibited by addition of cellobiose (C-7252, Sigma). EGI containing liquid is added in an appropriate dilution to a buffer containing 50 mM sodium acetate buffer (pH 5), 0.6 mM MUC and 4.6 mM cellobiose. The mixture is heated to 50° C. The reaction is stopped after ten minutes using 2% $Na_2CO_3$, pH 10. Purified CBHI is detected using the same assay as for EGI without the addition of the inhibitor cellobiose.

The partition coefficient K is defined as the ratio of the measured concentrations or activities in the top and bottom phase respectively.

The Yield Y is defined as follows:

$$Y_T = \frac{1}{1 + \left[\frac{V_B}{V_T} \cdot \frac{1}{K}\right]}$$

where $Y_T$ is the Yield of the top phase, $V_B$ and $V_T$ are the volumes of top and bottom phase respectively. The Yield of the bottom phase can be described accordingly.

The mass balances, e.g. recovery of all added protein, are always checked for completeness to ensure no artificially high Yield (e.g. due to possible inactivation of the protein in the bottom phase). The values are usually calculated based on total enzyme activity (EGI wt plus the EGI-fusion) and thus the values are underestimated for the separation of the fusion.

Example 10

Production of HFBI-Single Chain Antibody Fusion Protein in *T. reesei* Δhfb2 Strain for Purification in ATPS A *T. reesei* strain is constructed which produces a fusion protein consisting of *T. reesei* HFBI protein in the N-terminus and in the C-terminus a single chain antibody (ENA5SCFV) recognizing a small molecular weight derivative of diarylalkyltriazole. The fusion is to be subjected for purification using aqueous two-phase system.

For cloning of the enantiospecific Fab-fragments against the diarylalkyltriazole antigen, total RNA was isolated using the extraction protocoll of Promega from the hybridoma cell line obtained from the spleen cells of mice immunized with antigen. The mRNA fraction was purified using the Oligotex-dT polyA+ purification kit of Qiagen and the cDNA synthesis was performed with AMV reverse transcriptase—system of Promega. The cDNA was then subjected to PCR amplification using primer mixtures specific for each antibody group, 9 for heavy chains and 4 for light chains (according to Kabat et. al., 1991, Sequences of proteins of immunological interest, NIH publication No. 91-3242). The polymerization was carried out using the Dynazyme polymerase (Finnzymes) and standard conditions according to the manufacturer's instructions. After the amplification, both the heavy and the light chains were cloned as a dicistronic operon under the tac promoter controlled by the lacI$^q$ repressor present in the expression vector pTI8 (Takkinen et al, 1991). For secretion, the PelB signal sequence of pectate lyase of *Erwinia carotovora* (Takkinen et al, 1991) was linked for both the heavy and the light chains. A six histidine tag was added to the C-termini of the light chains. The resulting plasmid is pENA5-His.

For construction of a ENA5SCFV single chain antibody, the variable domains of the heavy and light chains were amplified with PCR using pENA5-His as template. The amplified fragment was cloned into pKKtac vector (Takkinen et al. 1991) resulting in pENA5SCFV. pENA5SCFV vector carries the coding region for ENA5SCFV single chain antibody consisting of the variable domains of the heavy and light chains connected via a glycine serine linker (Huston et al 1988 and 1991) and a 6× histidine tag at the C-terminal end. Transcription and secretion of the single chain antibody are under control of the tac promoter and pelB signal sequence, respectively (Takkinen et al. 1991).

Figure 6:
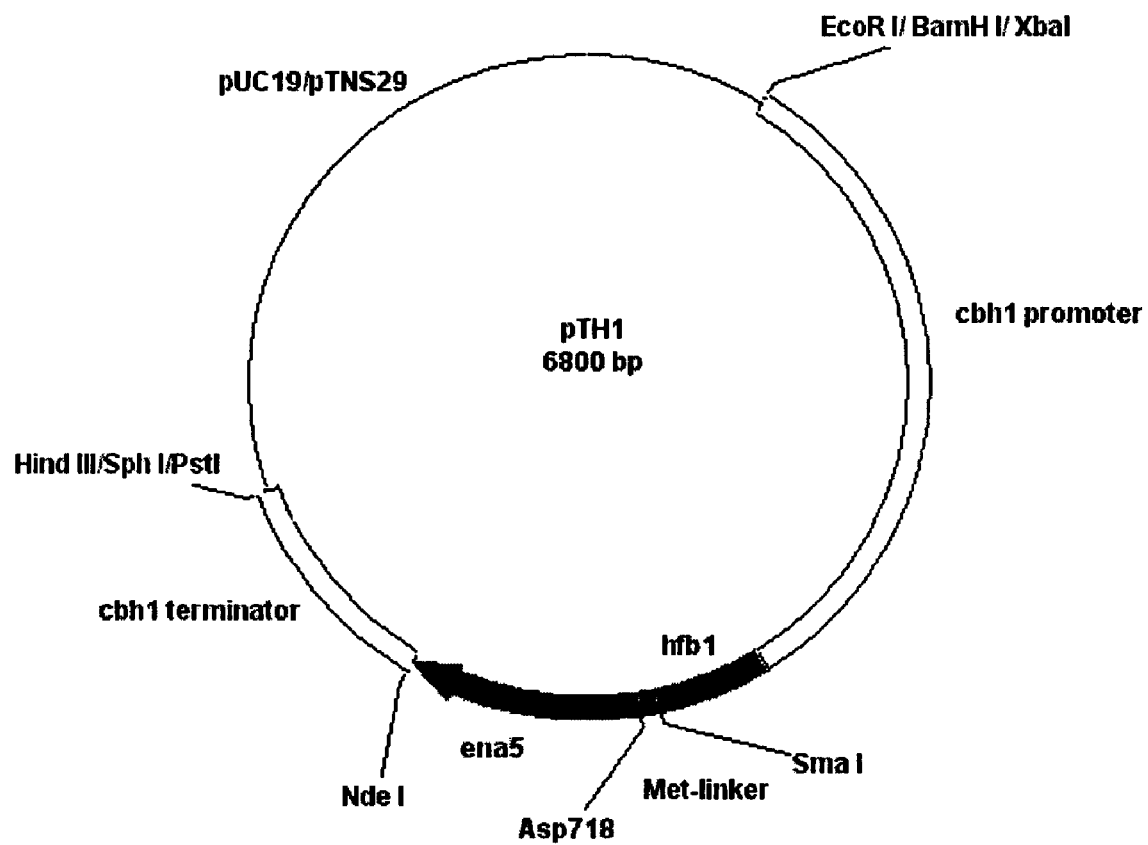
FIG. 6 depicts plasmid pTH1

For construction of HFBI-ENA5SCFV fusion protein, pENA5SCFV was digested with NcoI and XbaI. The fragment containing the ena5scfv gene and the histidine tail (6×His) was blut-end cloned to pTNS29 resulting in pTH1 (FIG. 6). pTNS29 vector carries the hfb1 coding region of *T. reesei* followed by a linker sequence (ProGlyAlaSerThr SerThrGlyMetGlyProGlyGly) (SEQ ID No 5) under the control of cbh1 promoter and terminator sequences.

Figure 7:
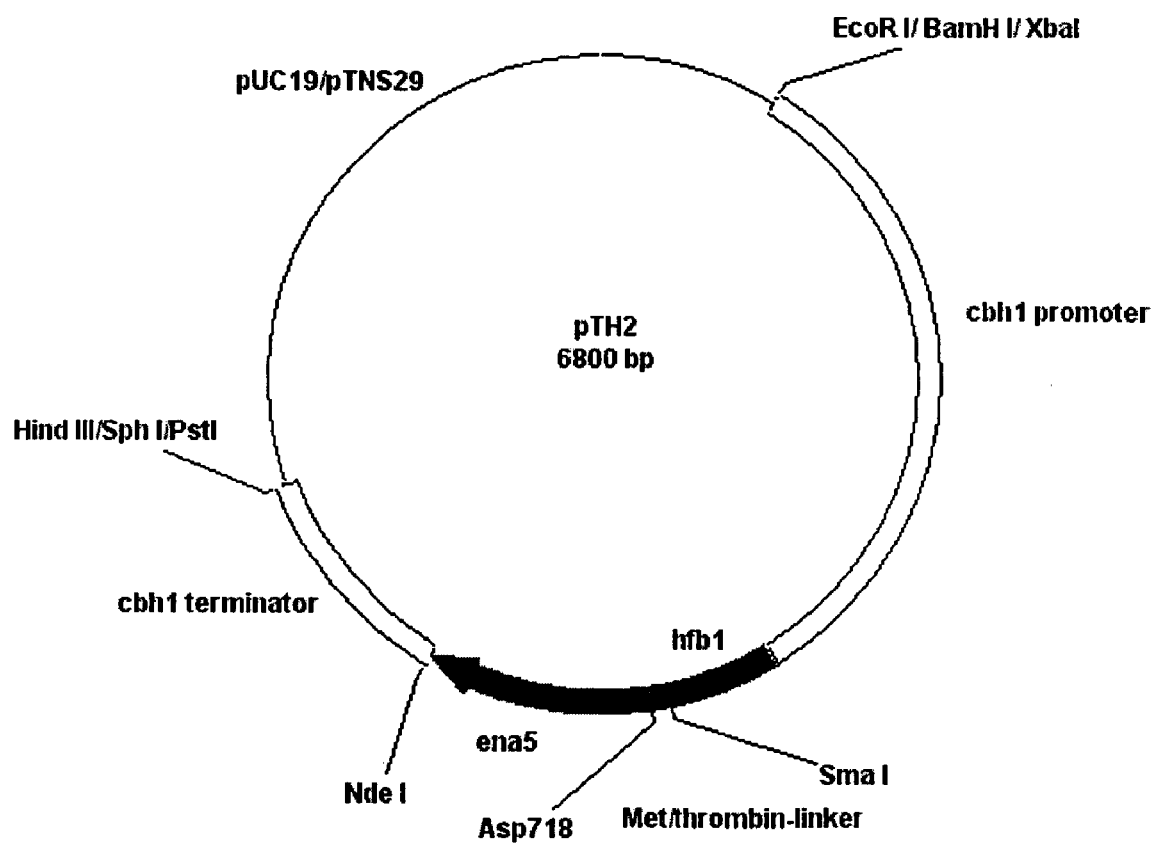
FIG. 7 depicts plasmid pTH2
Figure 8A:
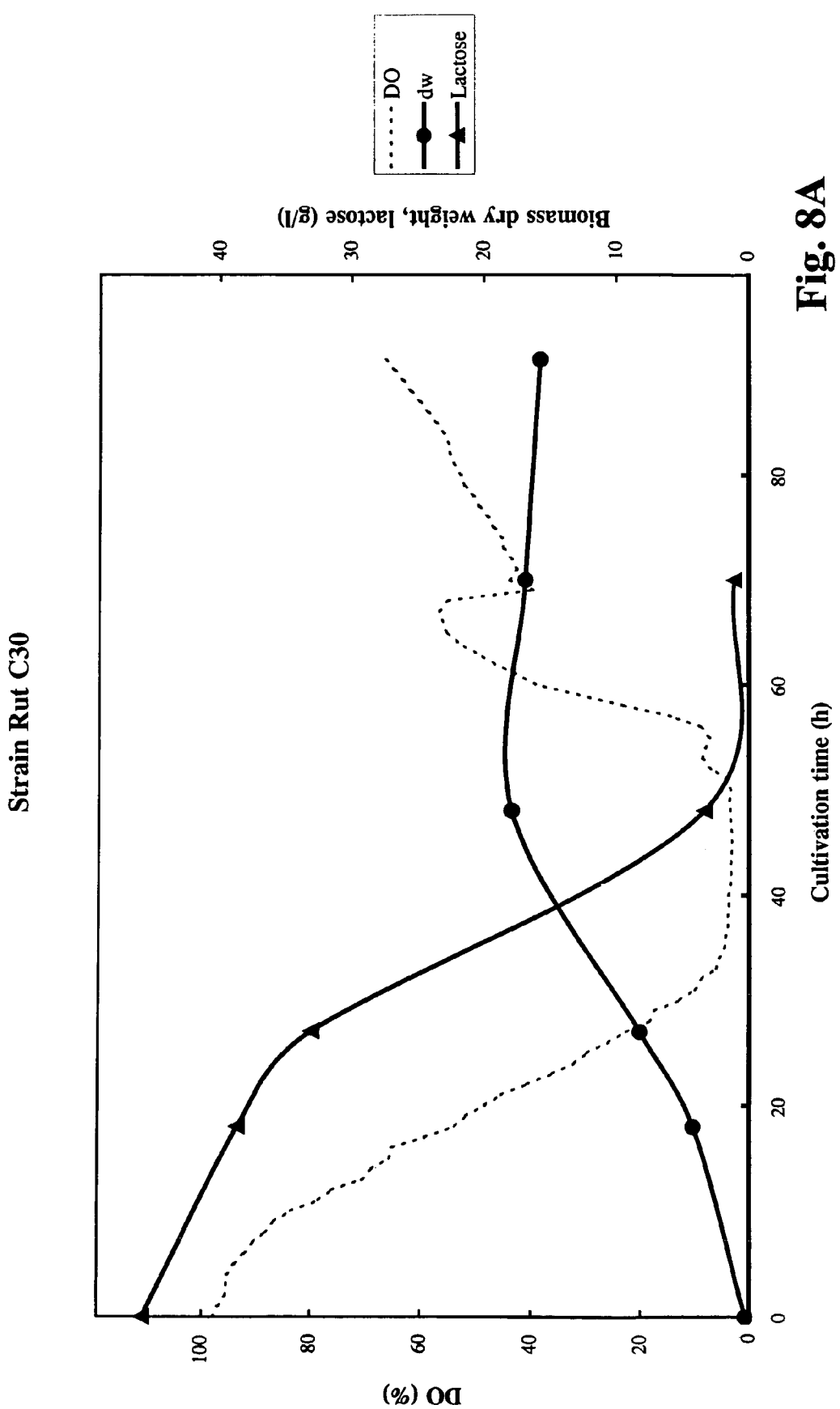
FIGS. 8 A and B depicts growth parameters of *Trichoderma* strains in a fermentor cultivation on lactose (DO=dissolved oxygen).
Figure 8B:
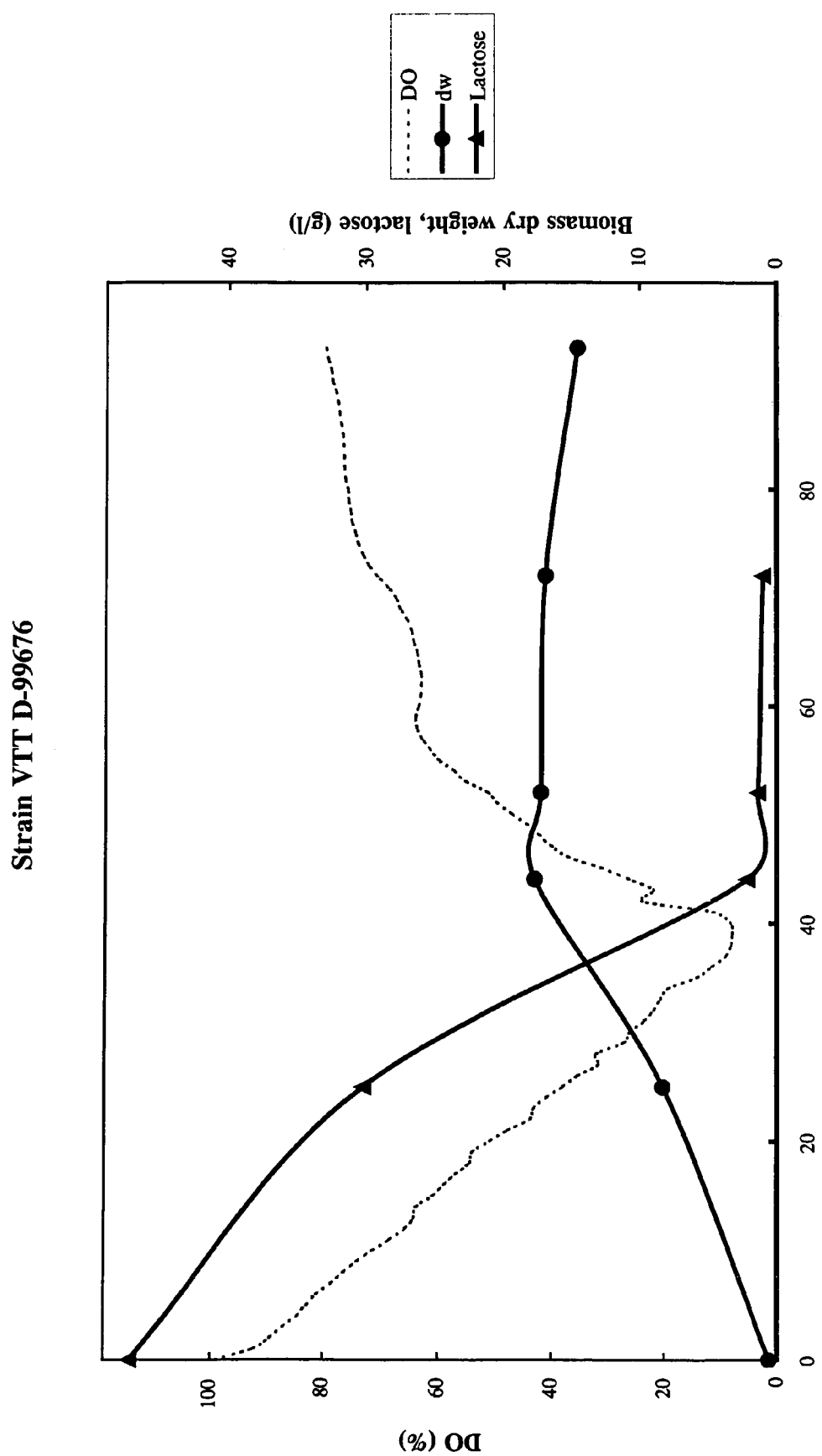
Figure 9A:
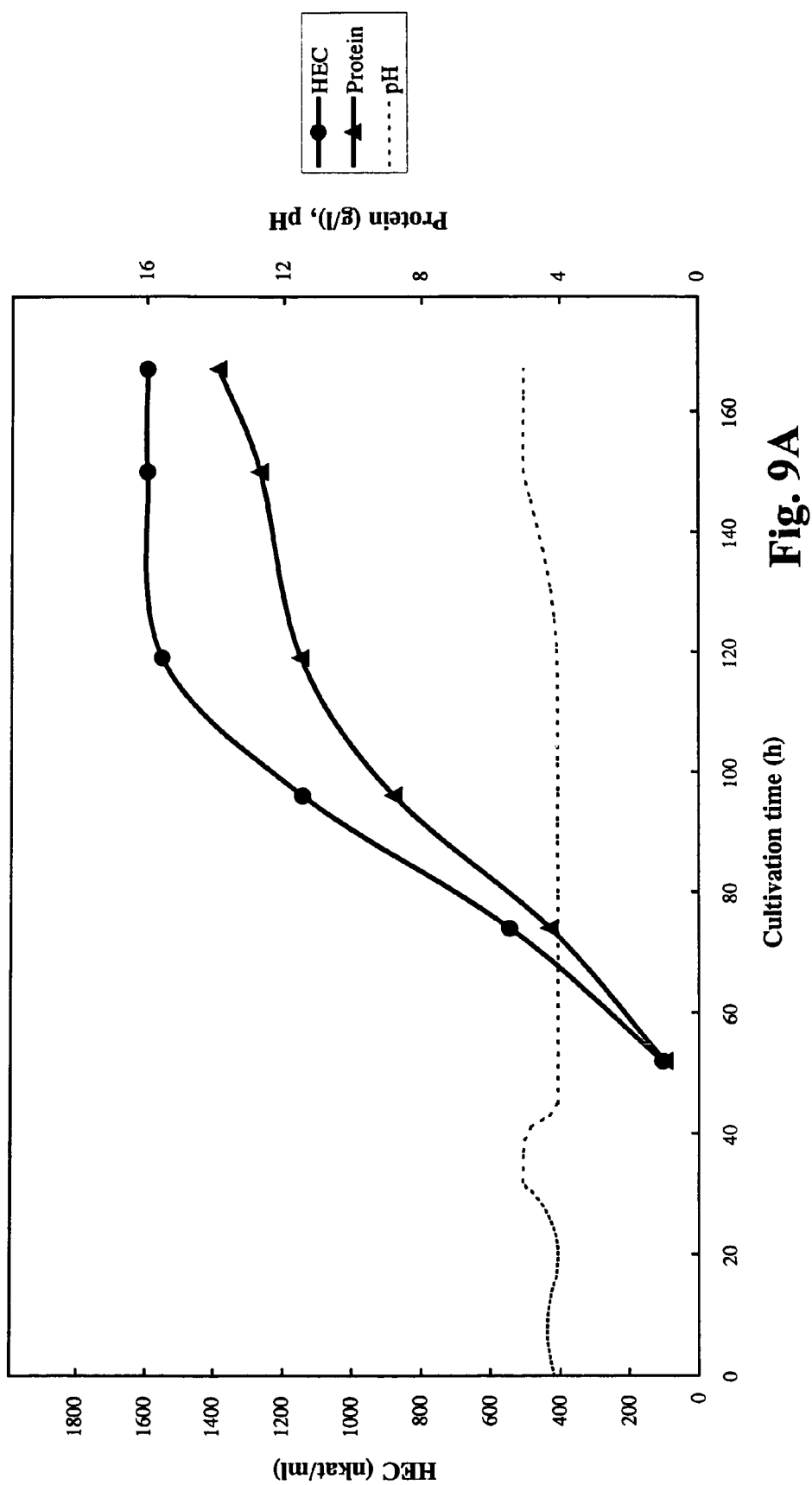
FIGS. 9A and B depicts the production of soluble protein in a fermentor cultivation on cellulose medium.
Figure 9B:
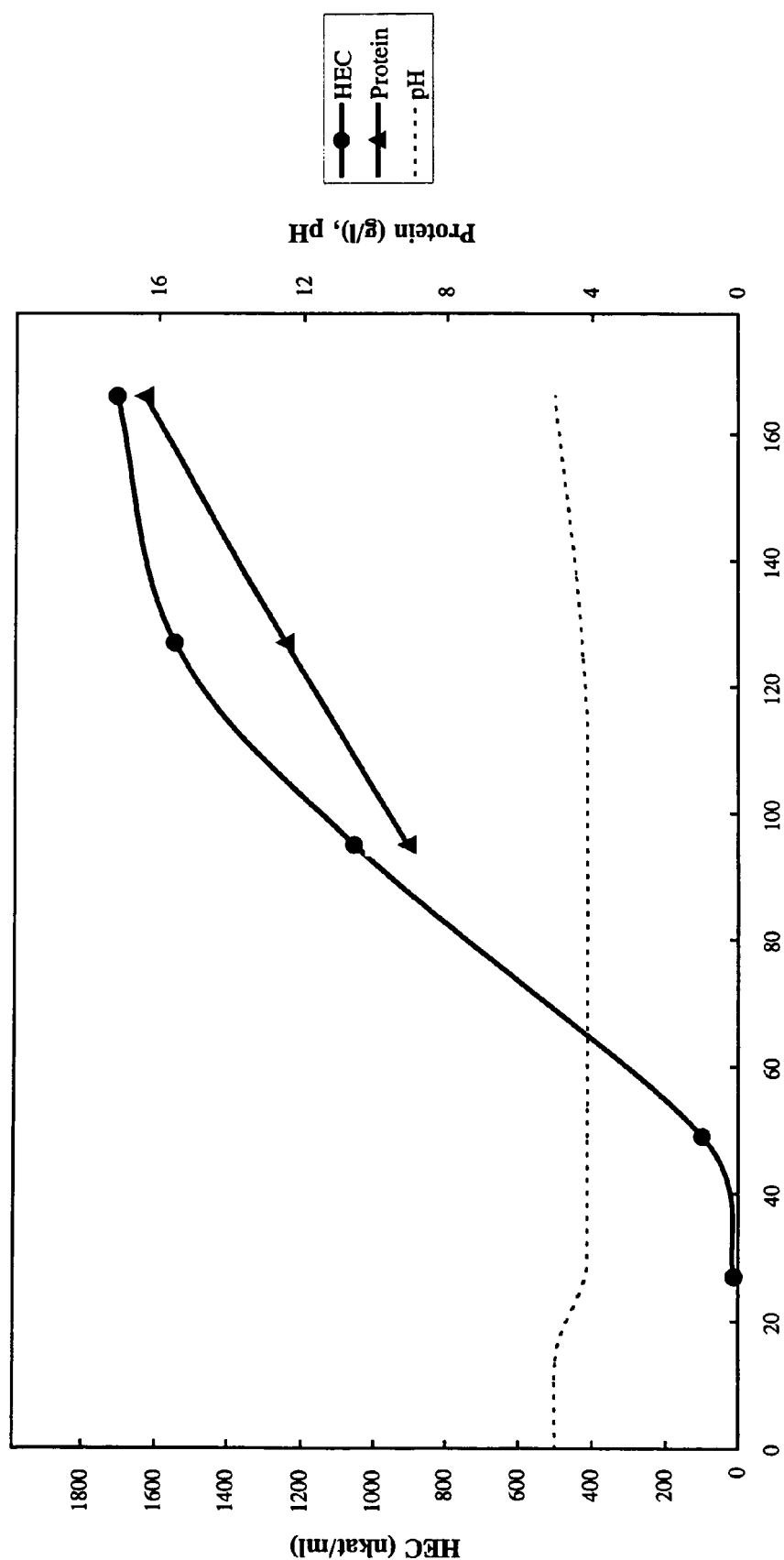

For construction of HFBI-ENA5SCFV fusion protein with a thrombin cleavage site in the linker peptide, ena5scfv coding region (from Ala-23 to the STOP codon) and a peptide linker containing the thrombin cleavage site (Gly Thr Leu Val Pro Arg Gly Pro Ala Glu Val Asn Leu Val) (SEQ ID No 6) preceeding it was amplified with PCR using pENA5SCFV as a template and as a 5' primer GAA TTC GGTACC CTC GTC CCT CGC GGT CCC GCC GAA GTG AAC CTG GTG (SEQ ID No 7) and as a 3' primer TGA ATT CCATATGCT AAC CCC GTT TCA TCT CCA G (SEQ ID No 8). The sequence in bold in the 5' primer encodes the first 6 N-terminal residues of ENA5SCFV. The sequence in italics is a thrombin cleavage site and underlined GGT ACC is Asp718 site. The sequence in bold in the 3' primer encodes the 6 C-terminal residues of ENA5SCFV and the underlined CA TATG is a NdeI site. The 790 bp PCR fragment was purified from agarose gel and ligated to pTNS29 resulting in pTH2 (FIG. 7).

*Trichoderma reesei* strain VTT-D-99726 (QM9414 Δhfb2) is co-transformed essentially as described (Penttilä et al., Gene (1987) 61:155-164) using 10 µg of the plasmids pTH1 and PTH2 and as selection plasmid 2 µg pTOC202. Amd+transformants obtained are streaked two times onto plates containing acetamide. Thereafter spore suspensions are made from transformants grown on Potato Dextrose agar (Difco).

The production of the two HFBI-ENA5SCFV fusion proteins is tested by Western analysis with HFBI specific antibody and with the antibody against the his-tail from shake flask cultivations carried out in minimal medium supplemented with 3% lactose or Solka flock cellulose and spent grain.

Partitioning experiments of the HFBI-ENA5 fusion proteins in ATPS using the polyoxyethylene detergent $C_{12-18}$ $EO_5$ (Agrimul NRE 1205, Henkel) with the supernatants of the best production strains obtained in this study and the control strain VTT-D-99726 (QM9414 Δhfb2) are carried out and analysed as described in Example 9.

REFERENCES

Arntz, C. and Tudzynski, P. (1997) Identification of genes induced in alkaloid-producing cultures of *Claviceps* sp. Curr. Genet. 31: 357-360.

Bailey, M. J., Biely, P. and Poutanen, K. (1992) Interlaboratory testing of methods for assays of xylanase activity. 23:257-270.

Cameotra, S. S. and Makkar, R. S. (1998) Synthesis of biosurfactants in extreme conditions. Appl. Microbiol. Biotechnol. 50:520-529.

Carpenter, C. E., Mueller, R. J., Kazmierczak, P., Zhang, L., Villalon, D. K. and VanAlften, N. K. (1992) Effect of a virus on accumulation of a tissue-specific cell surface protein of the fungus *Cryphonectria* (*Endothia*) *parasitica*. Mol. Plant-Microbe Interact. 4:55-61.

de Vries, O. M. H., Fekkes, M. P., Wösten, H. A. B. and Wessels, J. G. H. (1993) Insoluble hydrophobin complexes in the walls of *Schizophyllum commune* and other filamentous fungi, Arch Microbiol. 159:330-335.

de Vries, O. M. H., Moore, S., Arntz, C, Wessels, J. G. H. and Tudzynski, P. (1999) Identification and characterization of a tri-partite hydrophobin from *Claviceps fusiformis* Eur. J. Biochem. 262:377-385.

Huston, J. S. et al. (1988) Proc. Natl. Acad. Sci. USA. 85:5879-5883.

Huston, J. S., Mudgett-Hunter, M., Tai, M.-S., McCartney, J., Warren, F.,

Haber, E. and Oppermann, H. (1991) Methods Enzymol. 203: 46-88.

Hyytiä, T., Selber, K., Qiao, M., Fagerström, R., Kula, M.-R., Nakari-Setälä, T. and Penttilä, M., (1999). A novel strategy for protein production and purification in *Trichoderma reesei*. 6th International *Trichoderma-Gliogladium* Workshop. Jun. 11-13, 1999. Hanasaari, Finland.

Kaartinen, M., Knowles, J. K. C. and Teeri, T. T. (1991) An active single-chain antibody containing a cellulase linker domain is secreted by *Escherichia coli*. Protein Eng. 4:837-841

Kershaw, M. J. and Talbot, N. J. (1998) Hydrophobins and repellents: proteins with fundamental roles in fungal morphogenesis. Fungal Gen. Biol. 23:18-33.

Lang, S, and Wullbrandt, D. (1999) Rhamnose lipids—biosynthesis, microbial production and application potential. Appl. Microbiol. Biotechnol. 51:22-32.

Lora, J. M., de la Cruz, J., Betitez, T., Liobell, A. and Pintor-Toro, J. A. (1994) A putative catabolite-repressed cell wall protein from the mycoparasitic fungus *Trichoderma harzianum*. Mol. Gen. Genet. 242:461-466.

Lora, J. M., Pintor-Toro, J. A., Benitez, T. and Romero, L. C. (1995) Mol. Microbiol. 18:377-382.

Lowry, O. H., Rosebrough, N. H., Parr, A. L. and Randell, R. J. (1951) Protein measurement with the Folin phenol reagent. J. Biol. Chem. 193:265-275

IUPAC (1997) Measurement of cellulase activities. Pure Appl. Chem. 59:257-268

Muñoz, G., Nakari-Setälä, T., Agosin, E. and Penttilä, M. (1997). Hydrophobin gene srh1, expressed during sporulation of the biocontrol agent *Trichoderma harzianum*. Curr. Genet. 32:225-230.

Nakari-Setälä, T., Aro, N., Kalkkinen, N., Alatalo, E. and Penttilä, M. (1996). Genetic and biochemical characterization of the *Trichoderma reesei* hydrophobin HFBI. Eur. J. Biochem. 235:248-255.

Nakari-Setälä, T., Aro, N., Ilmén, M., Muñoz, G., Kalkkinen, N. and Penttilä, M. (1997). Differential expression of the vegetative and spore-bound hydrophobins of *Trichoderma reesei*: cloning and characterization of the hfb2 gene. Eur. J. Biochem. 248:415-423.

Richter, M., Willey, J. M., Süssmuth, R., Jung, G. and Fiedler, H.-P. (1998) Streptofactin, a novel biosurfactant with aerial mycelium inducing activity from *Streptomyces tendae*. FEMS Microbiol Lett 163:165-171.

Schuren, F. H. J. and Wessels, J. G. H. (1990) Two genes specifically expressed in fruiting dikaryons of *Schizsophyllum commune*: homologgies with gene not regulated by mating-type genes. Gene 90:199-205.

Russo, P. S., Blum, F. D., Ipsen, J. D., Miller, W. G. and Abul-Haki, Y. J. (1992) The surface activity of the phytotoxin cerato-ulmin. Can. J. Bot. 60:1414-1422.

Takkinen, K., Laukkanen, M.-L., Sizmann, D., Alfthan, K., Immonen, T., Vanne, L., Van der Vegt, W., van der Mei, H. C., Wösten, H. A. B., Wessels, J. G. H. and Busscher, H. J. (1996) A comparison of the surface activity of the fungal hydrophobin SC3p with those of other proteins. Biophys Chem. 51:253-260.

Van Tilbeurgh, H., Loonties, F. G., De Bruyne, C. K. and Clayessens, M. (1988). Methods Enzymol. 160:45-59.

Wessels, J. G. H. (1994) Developmental regulation of fungal cell wall formation. Ann. Rev. Phytopathol. 32:413-437.

Wessels, J. G. H. (1997). Hydrophobins: proteins that change the nature of the fungal surface. Adv. Microbial Physiol. 38:1-45.

Wessels, J. G. H, de Vries O. M. H., Åsgeirsdottir, S. A. and Schuren F. H. J. (1991a) Hydrophobin genes involved in formation of aerial hyphae and fruit bodies in *Schizophyllum commune*. Plant Cell 3:793-799.

Wessels, J. G. H, de Vries O. M. H., Åsgeirsdottir, S. A. and Springer, J. (1991b) The thn mutation of *Scizophyllum commune*, which suppresses formation of aerial hyphae, affects expression of the Sc3 hydrophobin gene. J. Gen. Microbiol. 137:2439-2445.

Willey, J. M., Santamaria, R., Guijarro, J., Geislich, M. and Losick, R. (1991) Extracellular complementation of a developmental mutation implicates a small sporulation protein in aerial mycelium formation by *S. coelicor*. Cell 65:641-650.

Wösten, H. A. B, de Vries, O. M. H. and Wessels, J. G. H. (1993) Interfacial self-assembly of a fungal hydrophobin into a hydrophobic rodlet layer. Plant Cell 5:1567-1574.

Wösten, H. A. B., Schuren, F. H. J. and Wessels, J. G. H. (1994a) Interfacial self-assembly of a hydrophobin into an amphipathic membrane mediates fungal attachment to hydrophobic surfaces. EMBO J. 13:5848-5854.

Wösten, H. A. B., Asgeirsdottir, S. A., Krook, J. H., Drenth, J. H. H. and Wessels, J. G. H. (1994b) The fungal hydrophobin S'C3p self-assembles at the surface of aerial hyphae as a protein membrane constituting the hydrophobic rodlet layer. Eur. J. Cell. Biol. 63:122-129.

Wösten, H. A. B and Wessels, J. G. W (1997) Hydrophobins, from molecular structure to multiple functions in fungal development. Mucoscience 38:363-374.

Wösten, H. A. B., van Wetter, A.-M., Lugones, L. G., van der Mei, H. C., Busscher, H. J. and Wessels, J. G. H. (1999) How a fungus escapes the water to grow into the air. Current Biology 9:85-88.

The invention claimed is:

1. A method for decreasing the foam formation during cultivation of *Trichoderma* production host, characterized in that the process comprises the steps of
   genetically modifying the *Trichoderma* production host in such way that the *Trichoderma* production host produces at least 50% less Hydrophobin I (HFBI) or Hydrophobin II (HFBII) or both during cultivation, compared to the non-modified parent host strain thereby producing a modified *Trichoderma* production host; and
   cultivating the modified *Trichoderma* production host under suitable culture conditions.

2. The method of claim 1 characterized in that the genetic modification comprises genetic modification of a DNA sequence encoding the HFBI or HFBII polypeptide.

3. The method of claim 1, characterized in that the genetic modification comprises genetic modification of the regulatory region of a gene encoding the HFBI or HFBII polypeptide.

4. The method of claim 1, characterized in that the genetic modification comprises genetic modification of a DNA sequence encoding the HFBI or HFBII polypeptide.

5. The method of claim 4, characterized in that genetic modification comprises inactivation of a DNA sequence encoding the HFBI or HFBII polypeptide.

6. The method of claim 5, characterized in that the genetic modification comprises deletion of a DNA sequence encoding the HFBI or HFBII polypeptide.

7. The method of claim 1, wherein said cultivation is carried out in the presence of agitation and/or aeration.

8. The method of claim 1, wherein said cultivation occurs in a fermentor.

9. The method of claim 8, wherein said fermentor is an airlift fermentor.

10. The method of claim 1, wherein the *Trichoderma* production host produces 60-80% less HFBI or HFBII or both during cultivation, compared to the non-modified parent host strain.

11. The method of claim 1, wherein the *Trichoderma* production host produces 80-100% less HFBI or HFBII or both during cultivation, compared to the non-modified parent host strain.

12. The method of claim 1, wherein the *Trichoderma* production host is *Trichoderma reesei*.

13. The method of claim 12, wherein the *Trichoderma* production host is *Trichoderma reesei* selected from the group consisting of QM9414 (VTT-D-74075), Rut-C30 (VTT-D-86271) and QM9414 Δhfb1 (VTT-D-99724).

14. A method for decreasing the foam formation during cultivation of a *Trichoderma reesei* production host, characterized in that the process comprises the steps of genetically modifying the *Trichoderma reesei* production host in such a way that the *Trichoderma reesei* production host produces at least 50% less Hydrophobin I (HFBI) or Hydrophobin II (HFBII) or both during cultivation, compared to the non-modified parent host strain thereby producing a modified *Trichoderma reesei* production host; and cultivating the modified *Trichoderma reesei* production host under suitable culture conditions in the presence of agitation and/or aeration in an airlift fermentor.

15. The method according to claim 14, wherein the *Trichoderma reesei* production host is *Trichoderma reesei* selected from the group consisting of QM9414 (VTT-D-74075), Rut-C30 (VTT-D-86271) and QM9414 Δhfb1 (VTT-D-99724).

16. The method according to claim 14, wherein the *Trichoderma reesei* production host produces 80-100% less HFBI or HFBII or both during cultivation, compared to the non-modified parent host strain.

17. The method according to claim 14, wherein the cultivation is performed in the absence of antifoaming agent.

* * * * *